US012678103B2

(12) United States Patent
Mitchell et al.

(10) Patent No.: US 12,678,103 B2
(45) Date of Patent: Jul. 14, 2026

(54) VASCULAR ACCESS DEVICES FOR MONITORING PATIENT HEALTH

(71) Applicant: Veris Health Inc., New York, NY (US)

(72) Inventors: James D. Mitchell, Walnut Creek, CA (US); Andrew A. Thoreson, Orono, MN (US); Theodore C. Johnson, Lake Forest Park, WA (US); Jayme Ormiston Coates, New Hartford, CT (US)

( * ) Notice: Subject to any disclaimer, the term of this patent is extended or adjusted under 35 U.S.C. 154(b) by 620 days.

(21) Appl. No.: 17/309,339

(22) PCT Filed: Nov. 20, 2019

(86) PCT No.: PCT/US2019/062483
§ 371 (c)(1),
(2) Date: May 19, 2021

(87) PCT Pub. No.: WO2020/106890
PCT Pub. Date: May 28, 2020

(65) Prior Publication Data
US 2022/0015708 A1     Jan. 20, 2022

Related U.S. Application Data

(60) Provisional application No. 62/809,689, filed on Feb. 24, 2019, provisional application No. 62/770,033, filed on Nov. 20, 2018.

(51) Int. Cl.
*A61B 5/00* (2006.01)
*A61B 5/0205* (2006.01)
(Continued)

(52) U.S. Cl.
CPC .......... *A61B 5/6865* (2013.01); *A61B 5/0031* (2013.01); *A61B 5/02055* (2013.01);
(Continued)

(58) Field of Classification Search
CPC . A61B 5/6865; A61B 5/0031; A61B 5/02055; A61B 5/0215; A61B 5/1118;
(Continued)

(56) References Cited

U.S. PATENT DOCUMENTS

| 4,834,720 A | 5/1989 | Blinkhorn |
| 4,846,191 A | 7/1989 | Brockway et al. |

(Continued)

FOREIGN PATENT DOCUMENTS

| AU | 691877 B2 | 5/1998 |
| CA | 2757836 C | 5/2017 |

(Continued)

OTHER PUBLICATIONS

Dubovitskaya, et al., "Secure and Trustable Electronic Medical Records Sharing using Blockchain", AMAI Annual Symposium Proceedings Achive, Jan. 1, 2017, pp. 650-659.
(Continued)

*Primary Examiner* — Paula J Stice

(57) ABSTRACT

An implantable vascular access device includes a fluid reservoir, a self-sealing cover disposed over the reservoir, and an outlet port configured to mate with a catheter, the outlet port fluidically coupled to the fluid reservoir. One or more sensors coupled to the device are configured to capture physiological data while the device is implanted within a patient. The device can also include a data communications unit configured to receive physiological data from the one or more sensors and transmit the physiological data to one or more remote computing devices. The device may also be inductively powered and/or can emit a localization signal in response to wireless interrogation.

20 Claims, 26 Drawing Sheets

(51) Int. Cl.
    *A61B 5/0215*     (2006.01)
    *A61B 5/11*     (2006.01)
    *A61B 5/145*     (2006.01)

(52) U.S. Cl.
    CPC .......... *A61B 5/0215* (2013.01); *A61B 5/1118*
    (2013.01); *A61B 5/14503* (2013.01); *A61B*
    *5/14542* (2013.01); *A61B 5/4839* (2013.01);
    *A61B 5/686* (2013.01); *A61B 2560/0219*
    (2013.01); *A61B 2560/0406* (2013.01); *A61B*
    *2562/168* (2013.01)

(58) Field of Classification Search
    CPC ............ A61B 5/14503; A61B 5/14542; A61B
    5/4839; A61B 5/686; A61B 2560/0219;
    A61B 2560/0406; A61B 2562/168; A61B
    5/0205; A61B 5/065; A61B 5/6867; A61B
    5/6876; A61B 5/00; A61M 2039/0238;
    A61M 2205/3523; A61M 39/0208; A61M
    2205/3327; A61M 2205/52
    See application file for complete search history.

(56) References Cited

U.S. PATENT DOCUMENTS

| | | | |
|---|---|---|---|
| 4,861,341 A | 8/1989 | Woodburn |
| 4,929,236 A | 5/1990 | Sampson |
| 5,167,638 A | 12/1992 | Felix et al. |
| 5,185,003 A | 2/1993 | Brethauer |
| 5,281,205 A | 1/1994 | McPherson |
| 5,360,407 A | 11/1994 | Leonard et al. |
| 5,399,168 A | 3/1995 | Wadsworth et al. |
| 5,423,334 A | 6/1995 | Jordan |
| 5,476,460 A | 12/1995 | Montalvo |
| 5,558,641 A | 9/1996 | Glantz et al. |
| 5,613,945 A | 3/1997 | Cai et al. |
| 5,620,419 A | 4/1997 | Lui et al. |
| 5,637,102 A | 6/1997 | Tolkoff et al. |
| 5,743,873 A | 4/1998 | Cai et al. |
| 5,833,654 A | 11/1998 | Powers et al. |
| 5,951,512 A | 9/1999 | Dalton |
| 5,989,216 A | 11/1999 | Johnson et al. |
| 6,086,555 A | 7/2000 | Eliasen et al. |
| 6,113,572 A | 9/2000 | Gailey et al. |
| 6,213,973 B1 | 4/2001 | Eliasen et al. |
| 6,296,615 B1 * | 10/2001 | Brockway ............... A61B 5/283 |
| | | 604/27 |
| 6,478,783 B1 | 11/2002 | Moorehead |
| 6,562,023 B1 | 5/2003 | Marrs et al. |
| 6,650,939 B2 | 11/2003 | Taepke et al. |
| 6,804,558 B2 | 10/2004 | Haller et al. |
| 6,847,844 B2 | 1/2005 | Sun et al. |
| 6,922,592 B2 | 7/2005 | Thompson et al. |
| 6,997,914 B2 | 2/2006 | Smith et al. |
| 7,037,273 B2 | 5/2006 | Zhu et al. |
| 7,069,086 B2 | 6/2006 | Von |
| 7,070,591 B2 | 7/2006 | Adams et al. |
| 7,177,684 B1 | 2/2007 | Kroll et al. |
| 7,181,505 B2 | 2/2007 | Haller et al. |
| D546,440 S | 7/2007 | Burnside |
| D556,153 S | 11/2007 | Burnside |
| 7,324,949 B2 | 1/2008 | Bristol |
| 7,347,843 B2 | 3/2008 | Adams et al. |
| 7,351,233 B2 | 4/2008 | Parks |
| D574,950 S | 8/2008 | Zawacki et al. |
| 7,445,614 B2 | 11/2008 | Bunodiere et al. |
| 7,479,107 B2 | 1/2009 | Zhu et al. |
| 7,713,251 B2 | 5/2010 | Tallarida et al. |
| 7,762,999 B2 | 7/2010 | Byrum |
| 7,775,966 B2 | 8/2010 | Dlugos et al. |
| 7,785,302 B2 | 8/2010 | Powers |
| 7,831,301 B2 | 11/2010 | Webb et al. |
| 7,844,341 B2 | 11/2010 | Von et al. |
| 7,909,769 B2 | 3/2011 | Zhu et al. |

| | | | |
|---|---|---|---|
| 7,909,804 B2 | 3/2011 | Stats |
| 7,942,863 B2 | 5/2011 | Kalpin et al. |
| 7,947,022 B2 | 5/2011 | Amin et al. |
| 7,959,615 B2 | 6/2011 | Stats et al. |
| 7,972,314 B2 | 7/2011 | Bizup et al. |
| 8,025,639 B2 | 9/2011 | Powers et al. |
| 8,029,482 B2 | 10/2011 | Maniar et al. |
| 8,057,401 B2 * | 11/2011 | Wolf .................... A61B 5/0086 |
| | | 600/561 |
| 8,092,435 B2 | 1/2012 | Beling et al. |
| 8,140,160 B2 | 3/2012 | Pless et al. |
| 8,147,455 B2 | 4/2012 | Butts et al. |
| 8,175,694 B2 | 5/2012 | Webb et al. |
| 8,177,762 B2 | 5/2012 | Beasley et al. |
| 8,202,259 B2 | 6/2012 | Evans et al. |
| 8,301,254 B2 | 10/2012 | Mosesov et al. |
| D676,955 S | 2/2013 | Orome |
| 8,382,724 B2 | 2/2013 | Maniar et al. |
| 8,391,981 B2 | 3/2013 | Mosesov |
| 8,396,803 B1 | 3/2013 | Dala et al. |
| 8,401,659 B2 | 3/2013 | Von et al. |
| 8,409,221 B2 | 4/2013 | Franklin et al. |
| 8,439,835 B1 | 5/2013 | Mckinley et al. |
| 8,475,417 B2 | 7/2013 | Powers et al. |
| 8,491,547 B2 | 7/2013 | Olsen et al. |
| 8,535,280 B2 | 9/2013 | Mitchell et al. |
| 8,535,281 B2 | 9/2013 | Travis et al. |
| 8,545,460 B2 | 10/2013 | Beasley et al. |
| 8,608,713 B2 | 12/2013 | Beasley et al. |
| 8,608,727 B2 | 12/2013 | Michels et al. |
| 8,615,305 B2 | 12/2013 | Von Arx et al. |
| 8,641,676 B2 | 2/2014 | Butts et al. |
| 8,641,688 B2 | 2/2014 | Powers et al. |
| 8,660,659 B2 | 2/2014 | Mosesov et al. |
| 8,744,581 B2 | 6/2014 | Mosesov |
| 8,805,478 B2 | 8/2014 | Powers et al. |
| 8,827,904 B2 | 9/2014 | Ball et al. |
| 8,920,389 B2 | 12/2014 | Kalpin et al. |
| 8,920,390 B2 | 12/2014 | Dalton et al. |
| 8,926,573 B2 | 1/2015 | Smith et al. |
| 8,932,271 B2 | 1/2015 | Hamatake et al. |
| 8,939,947 B2 | 1/2015 | Maniar et al. |
| 9,011,388 B2 | 4/2015 | Schwartz et al. |
| 9,017,256 B2 | 4/2015 | Gottesman |
| 9,072,881 B2 | 7/2015 | Dalton et al. |
| 9,079,004 B2 | 7/2015 | Wiley et al. |
| 9,101,264 B2 | 8/2015 | Acquista |
| 9,186,455 B2 | 11/2015 | Moyer |
| D748,249 S | 1/2016 | Pittet et al. |
| 9,248,268 B2 | 2/2016 | Wiley et al. |
| 9,327,106 B2 | 5/2016 | Beling et al. |
| 9,358,378 B2 | 6/2016 | Hanson et al. |
| 9,421,352 B2 | 8/2016 | Butts et al. |
| 9,474,888 B2 | 10/2016 | Wiley et al. |
| 9,485,883 B2 | 11/2016 | Koyama |
| 9,498,130 B2 | 11/2016 | Najafi et al. |
| 9,579,496 B2 | 2/2017 | Evans et al. |
| 9,603,992 B2 | 3/2017 | Powers |
| 9,603,993 B2 | 3/2017 | Powers |
| 9,642,556 B2 | 5/2017 | Mo et al. |
| 9,681,825 B2 | 6/2017 | Acquista |
| 9,717,895 B2 | 8/2017 | Wiley et al. |
| 9,814,833 B2 | 11/2017 | Kalpin |
| 9,821,150 B2 | 11/2017 | Pamment |
| 9,937,337 B2 | 4/2018 | Powers et al. |
| 9,950,150 B2 | 4/2018 | Beling et al. |
| 10,016,585 B2 | 7/2018 | Powers et al. |
| 10,022,094 B2 | 7/2018 | Kerr et al. |
| 10,052,470 B2 | 8/2018 | Powers et al. |
| 10,052,471 B2 | 8/2018 | Hamatake et al. |
| 10,086,186 B2 | 10/2018 | Evans et al. |
| 10,155,101 B2 | 12/2018 | Wiley et al. |
| 10,207,095 B2 | 2/2019 | Barron et al. |
| 10,307,581 B2 | 6/2019 | Hibdon et al. |
| 10,321,292 B2 | 6/2019 | Pflugh et al. |
| 11,096,582 B2 | 8/2021 | Mitchell et al. |
| 2001/0027331 A1 | 10/2001 | Thompson |
| 2002/0052539 A1 | 5/2002 | Haller et al. |
| 2002/0193846 A1 | 12/2002 | Pool et al. |

(56)     References Cited

U.S. PATENT DOCUMENTS

| | | | |
|---|---|---|---|
| 2003/0014091 A1 | 1/2003 | Rastegar et al. | |
| 2004/0054352 A1* | 3/2004 | Adams | A61B 5/318 |
| | | | 600/485 |
| 2005/0124980 A1 | 6/2005 | Sanders | |
| 2006/0116648 A1 | 6/2006 | Hamatake | |
| 2006/0178617 A1* | 8/2006 | Adams | A61B 5/0028 |
| | | | 128/903 |
| 2006/0178648 A1 | 8/2006 | Barron et al. | |
| 2007/0016089 A1 | 1/2007 | Fischell et al. | |
| 2007/0078391 A1* | 4/2007 | Wortley | A61M 39/0208 |
| | | | 604/116 |
| 2007/0135765 A1 | 6/2007 | Miller et al. | |
| 2007/0270672 A1 | 11/2007 | Hayter | |
| 2008/0114308 A1 | 5/2008 | Di et al. | |
| 2009/0118683 A1 | 5/2009 | Hanson et al. | |
| 2009/0131767 A1* | 5/2009 | Arne | A61B 5/6876 |
| | | | 623/1.1 |
| 2009/0227951 A1 | 9/2009 | Powers et al. | |
| 2010/0191166 A1 | 7/2010 | Phillips et al. | |
| 2010/0274221 A1 | 10/2010 | Sigg et al. | |
| 2011/0184342 A1 | 7/2011 | Pesach et al. | |
| 2011/0202041 A1 | 8/2011 | Forsell | |
| 2011/0213309 A1* | 9/2011 | Young | A61M 39/0208 |
| | | | 604/93.01 |
| 2012/0172711 A1 | 7/2012 | Kerr et al. | |
| 2012/0245439 A1 | 9/2012 | Andre et al. | |
| 2013/0150811 A1 | 6/2013 | Horgan | |
| 2014/0088519 A1 | 3/2014 | Kerr | |
| 2014/0207086 A1 | 7/2014 | Stats et al. | |
| 2014/0236105 A1 | 8/2014 | Hanson et al. | |
| 2014/0249503 A1 | 9/2014 | Bennett et al. | |
| 2015/0025478 A1 | 1/2015 | Hibdon et al. | |
| 2015/0112315 A1 | 4/2015 | Cudak et al. | |
| 2016/0317797 A1 | 11/2016 | Smith et al. | |
| 2017/0028185 A1 | 2/2017 | Wiley et al. | |
| 2017/0035396 A1* | 2/2017 | Solomon | A61K 31/198 |
| 2017/0340872 A1 | 11/2017 | Hanson et al. | |
| 2018/0043149 A1 | 2/2018 | Martin | |
| 2018/0078751 A1* | 3/2018 | Fedor | A61B 17/3423 |
| 2018/0103859 A1 | 4/2018 | Provenzano | |
| 2018/0147343 A1 | 5/2018 | Tyson | |
| 2018/0161565 A1 | 6/2018 | Maniar et al. | |
| 2018/0177982 A1 | 6/2018 | Albany et al. | |
| 2018/0193626 A1 | 7/2018 | Beling et al. | |
| 2018/0263511 A1 | 9/2018 | Burnes et al. | |
| 2019/0054284 A1 | 2/2019 | Smith et al. | |
| 2020/0155003 A1 | 5/2020 | Mitchell et al. | |
| 2020/0179669 A1 | 6/2020 | Mitchell et al. | |
| 2021/0361166 A1 | 11/2021 | Mitchell et al. | |
| 2021/0402164 A1 | 12/2021 | Mitchell et al. | |

FOREIGN PATENT DOCUMENTS

| | | |
|---|---|---|
| CN | 104740765 B | 3/2017 |
| DE | 102011078711 A1 | 1/2013 |
| EP | 0392199 A1 | 10/1990 |
| EP | 1391218 A3 | 4/2004 |
| EP | 1413329 B1 | 12/2005 |
| EP | 1773448 A1 | 4/2007 |
| EP | 1962921 A2 | 9/2008 |
| EP | 2020945 B1 | 2/2013 |
| EP | 2859911 A1 | 4/2015 |
| EP | 1874393 B1 | 9/2017 |
| EP | 2416828 B1 | 2/2018 |
| EP | 2501294 B1 | 8/2018 |
| ES | 2041000 T3 | 11/1993 |
| ES | 2041461 T3 | 11/1993 |
| ES | 2136613 T3 | 12/1999 |
| JP | 2000513952 A | 10/2000 |
| JP | 4795523 B2 | 11/2000 |
| JP | 2005169113 A | 6/2005 |
| JP | 4947876 B2 | 3/2012 |
| JP | 2016504158 A | 2/2016 |
| WO | 9934859 A1 | 7/1999 |
| WO | 2010118144 A1 | 10/2010 |
| WO | 2015097255 A2 | 7/2015 |
| WO | 2018/217633 A1 | 11/2018 |
| WO | 2019118929 A1 | 6/2019 |
| WO | 2020/106890 A1 | 5/2020 |
| WO | 2020106804 A1 | 5/2020 |
| WO | 2020106842 A1 | 5/2020 |
| WO | 2021102467 | 5/2021 |
| WO | 2022/140766 A1 | 6/2022 |

OTHER PUBLICATIONS

International Search Report and Written Opinion mailed Feb. 18, 2020; International Application No. PCT/US2019/062483; 12 pages.

Kuo et al., "Blockcain distributed ledger technologies for biomedical and health care applications", Journal of the American Medical Informatics Association, vol. 24, No. 6, Sep. 8, 2017, pp. 1211-1220.

* cited by examiner

VASCULAR ACCESS DEVICES FOR MONITORING PATIENT HEALTH

CROSS-REFERENCE TO RELATED APPLICATIONS

The present application is a 371 U.S. national phase application of International Patent Application No. PCT/US2019/062483, filed Nov. 20, 2019, which claims the benefit of priority of U.S. Provisional Application No. 62/770,033, filed Nov. 20, 2018, and U.S. Provisional Application No. 62/809,689, filed Feb. 24, 2019, each of which is hereby incorporated by reference in its entirety.

TECHNICAL FIELD

The present technology relates to implantable medical devices and associated systems and methods of use. In particular, the present technology is directed to vascular access devices, systems, and methods for monitoring patient health.

BACKGROUND

Vascular access devices (e.g., vascular access ports) are minimally invasive, surgically implanted devices that provide relatively quick and easy access to a patient's central venous system for the purpose of administering intravenous medications, such as chemotherapeutic agents. Conventional vascular access devices are commonly used for patients requiring frequent, repeated intravenous administration of therapeutic agents or fluid, repeated blood draws, and/or for patients with difficult vascular access.

Vascular access devices such as vascular access ports typically include a reservoir attached to a catheter. The entire unit is placed completely within a patient's body using a minimally invasive surgical procedure. In most cases the reservoir is placed in a small pocket created in the upper chest wall just inferior to the clavicle, and the catheter is inserted into the internal jugular vein or the subclavian vein with the tip resting in the superior vena cava or the right atrium. However, such vascular access devices can be placed in other parts of the body and/or with the catheter positioned in alternative sites as well. In conventional devices, the reservoir is typically bulky such that the overlying skin protrudes, allowing a clinician to use palpation to localize the device for access when it is to be used for a medication infusion or aspiration of blood for testing. A self-sealing cover (e.g., a thick silicone membrane) is disposed over and seals the reservoir, allowing for repeated access using a non-coring (e.g., Huber type) needle that is inserted through the skin and into the port. This access procedure establishes a system in which there is fluid communication between the needle, the vascular access device, the catheter, and the vascular space, thereby enabling infusion of medication or aspiration of blood via a transcutaneous needle.

Conventional vascular access devices are bulky by design to allow a clinician to localize the device by palpation. To be accurately accessed by a clinician, the vascular access device needs to be either visualized or palpated under the skin. Additionally, conventional vascular access ports have no electronic components and no internal power source. Accordingly, there is a need for improved vascular access devices.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology relates to implantable medical devices such as vascular access devices and associated systems and methods of use. Specific details of several embodiments of the technology are described below with reference to FIGS. 1-22.

The vascular access devices and systems of the present technology may be equipped with electronic components that provide a platform for remote patient monitoring. For example, the vascular access devices disclosed herein may include a sensing element configured to obtain patient physiological data while the vascular access device is implanted within the patient, and determine one or more physiological parameters based on the data. The system may determine certain physiological parameters, for example, that indicate one or more symptoms of a medical condition that requires immediate medical attention or hospitalization. Such physiological parameters can include those related to temperature, patient movement/activity level, heart rate, respiratory rate, blood oxygen saturation, and/or other suitable parameters described herein. Based on these parameters, the system may provide an indication to the patient and/or clinician that the patient has contracted or is at risk of contracting an illness or is experiencing complications from therapy. The system of the present technology may be especially beneficial for cancer patients undergoing chemotherapy, as chemotherapy has many side effects that could be fatal to the patient if not treated immediately. The vascular access devices, systems, and methods disclosed herein enable early detection of known symptoms, thereby improving patient survival rates and overall quality of life.

Additionally, the implanted device may contain data storage and communication technology that not only monitors physiologic parameters and logs device communication history, but also contains information about the patient's demographics, diagnoses, treatment history, and POLST (Physician Order for Life Sustaining Treatment) status. In some embodiments, the vascular access device can be configured for wireless communication with an interrogation device or other remote computing device. The interrogation device may also wirelessly recharge a battery of the vascular access device, for example via inductive charging.

Patient Monitoring System Overview

Figure 1:
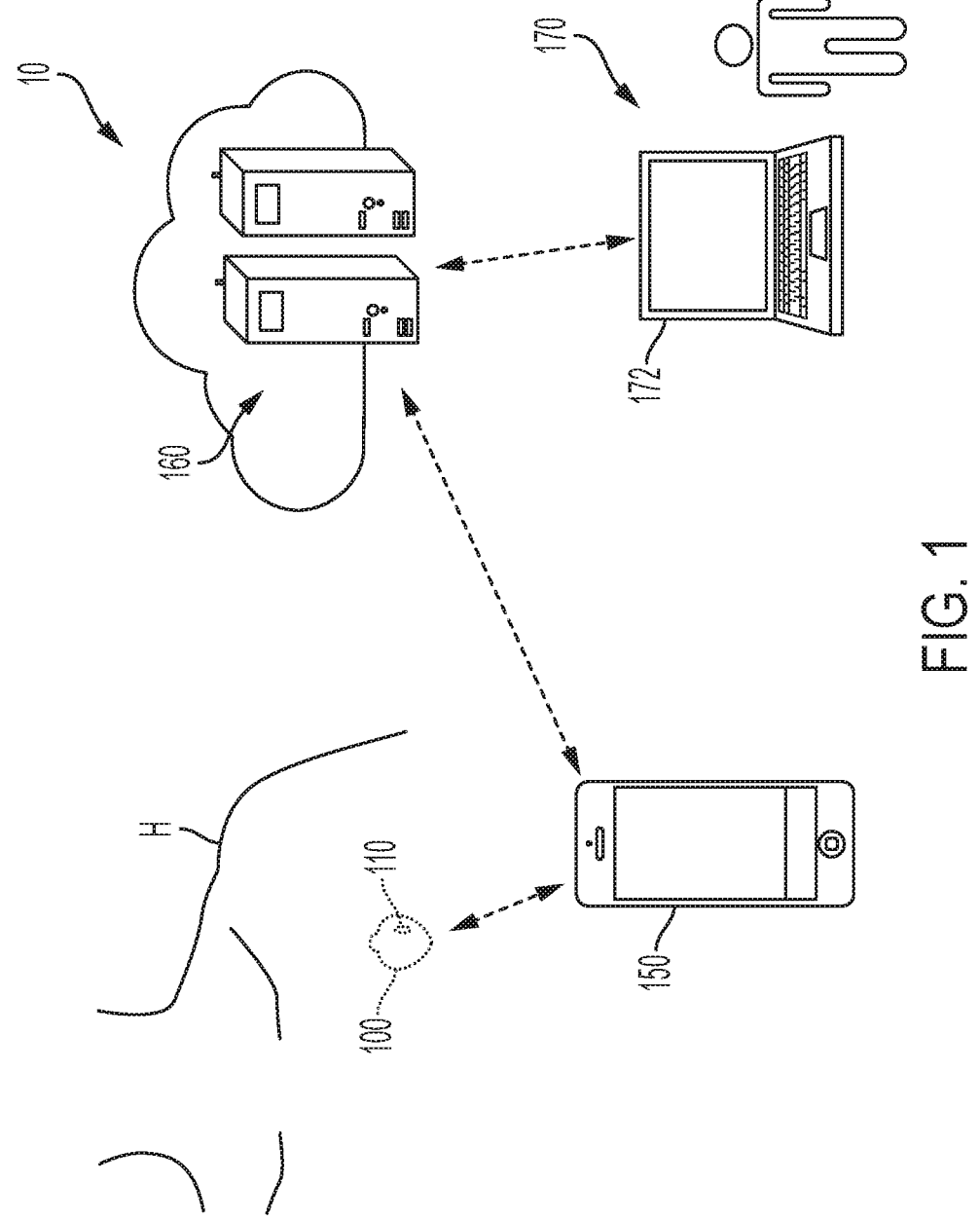
FIG. 1 is a schematic representation of a system for monitoring the health of a patient via an implanted medical device in accordance with the present technology.

FIG. 1 is a schematic representation of a system 10 for monitoring the health of a patient via a vascular access device 100 (or "device 100") in accordance with the present technology. The device 100 is configured to be implanted within a human patient H, such as at a subcutaneous location along an upper region of the patient's chest. As shown in FIG. 1, the device 100 may include a sensing element 110 configured to obtain physiological measurements that are used by the system 10 to determine one or more physiological parameters indicative of the patient's health. In some embodiments, the system 10 may detect a medical condition (such as sepsis) or associated symptom(s) based on the physiological parameter(s) and provide an indication of the detected condition to the patient, caregiver, and/or medical care team.

As shown schematically in FIG. 1, the device 100 may be configured to communicate wirelessly with a local computing device 150, which can be, for example, a smart device (e.g., a smartphone, a tablet, or other handheld device having a processor and memory), a special-purpose interrogation device, or other suitable device. Communication between the device 100 and the local computing device 150 can be mediated by, for example, near-field communication (NFC), infrared wireless, Bluetooth, ZigBee, Wi-Fi, inductive coupling, capacitive coupling, or any other suitable wireless communication link. The device 100 may transmit data including, for example, physiological measurements obtained via the sensing element 110, patient medical records, device performance metrics (e.g., battery level, error logs, etc.), or any other such data stored by the device 100. In some embodiments, the transmitted data is encrypted or otherwise obfuscated to maintain security during transmission to the local computing device 150. The local computing device 150 may also provide instructions to the vascular access device 100, for example to obtain certain physiological measurements via the sensing element 110, to emit a localization signal, or to perform other functions. In some embodiments, the local computing device 150 may be configured to wirelessly recharge a battery of the device 100, for example via inductive charging.

The system 10 may further include first remote computing device(s) 160 (or server(s)), and the local computing device 150 may in turn be in communication with first remote computing device(s) 160 over a wired or wireless communications link (e.g., the Internet, public and private intranet, a local or extended Wi-Fi network, cell towers, the plain old telephone system (POTS), etc.). The first remote computing device(s) 160 may include one or more own processor(s) and memory. The memory may be a tangible, non-transitory computer-readable medium configured to store instructions executable by the processor(s). The memory may also be configured to function as a remote database, i.e., the memory may be configured to permanently or temporarily store data received from the local computing device 150 (such as one or more physiological measurements or parameters and/or other patient information).

In some embodiments, the first remote computing device(s) 160 can additionally or alternatively include, for example, server computers associated with a hospital, a medical provider, medical records database, insurance company, or other entity charged with securely storing patient data and/or device data. At a remote location 170 (e.g., a hospital, clinic, insurance office, medical records database, operator's home, etc.), an operator may access the data via a second remote computing device 172, which can be, for example a personal computer, smart device (e.g., a smartphone, a tablet, or other handheld device having a processor and memory), or other suitable device. The operator may access the data, for example, via a web-based application. In some embodiments, the obfuscated data provided by the device 100 can be de-obfuscated (e.g., unencrypted) at the remote location 170.

In some embodiments, the device 100 may communicate with remote computing devices 160 and/or 172 without the intermediation of the local computing device 150. For example, the vascular access device 100 may be connected via Wi-Fi or other wireless communications link to a network such as the Internet. In other embodiments, the device 100 may be in communication only with the local computing device 150, which in turn is in communication with remote computing devices 160 and/or 172.

Figure 2:
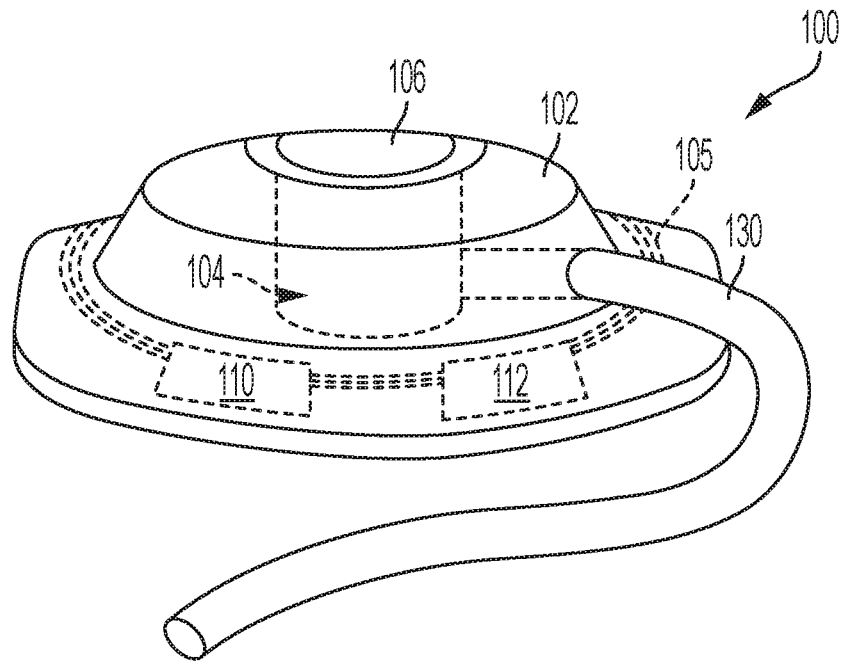
FIG. 2 shows an example of a vascular access device configured for use with the system of FIG. 1.

FIG. 2 shows an example of a vascular access device 100 (or "device 100") configured for use with the system 10 of the present technology. As shown in FIG. 2, the device 100 comprises a housing 102 configured to be implanted within a human patient, a fluid reservoir 104 contained within the housing 102, and a septum 106 adjacent the reservoir 104 and configured to receive a needle therethrough for delivery of a fluid (such as a therapeutic or diagnostic agent) to the reservoir 104 (as described in greater detail below with respect to FIG. 3). The housing 102 may be made of a biocompatible plastic, metal, ceramic, medical grade silicone, or other material that provides sufficient rigidity and strength to prevent needle puncture. The septum 106 can be, for example, a self-sealing membrane made of silicone or other deformable, self-sealing, biocompatible material. In some embodiments, the device 100 may include a catheter 130 that extends distally from the housing 102 and is in fluid communication with the reservoir 104. For example, the catheter 130 can be configured to mate with an outlet port of the device 100 via a barb connector or other suitable mechanical connection. The catheter 130 may be a single or multi-lumen catheter. In some embodiments, the device 100 includes multiple separate catheters.

Figure 3:
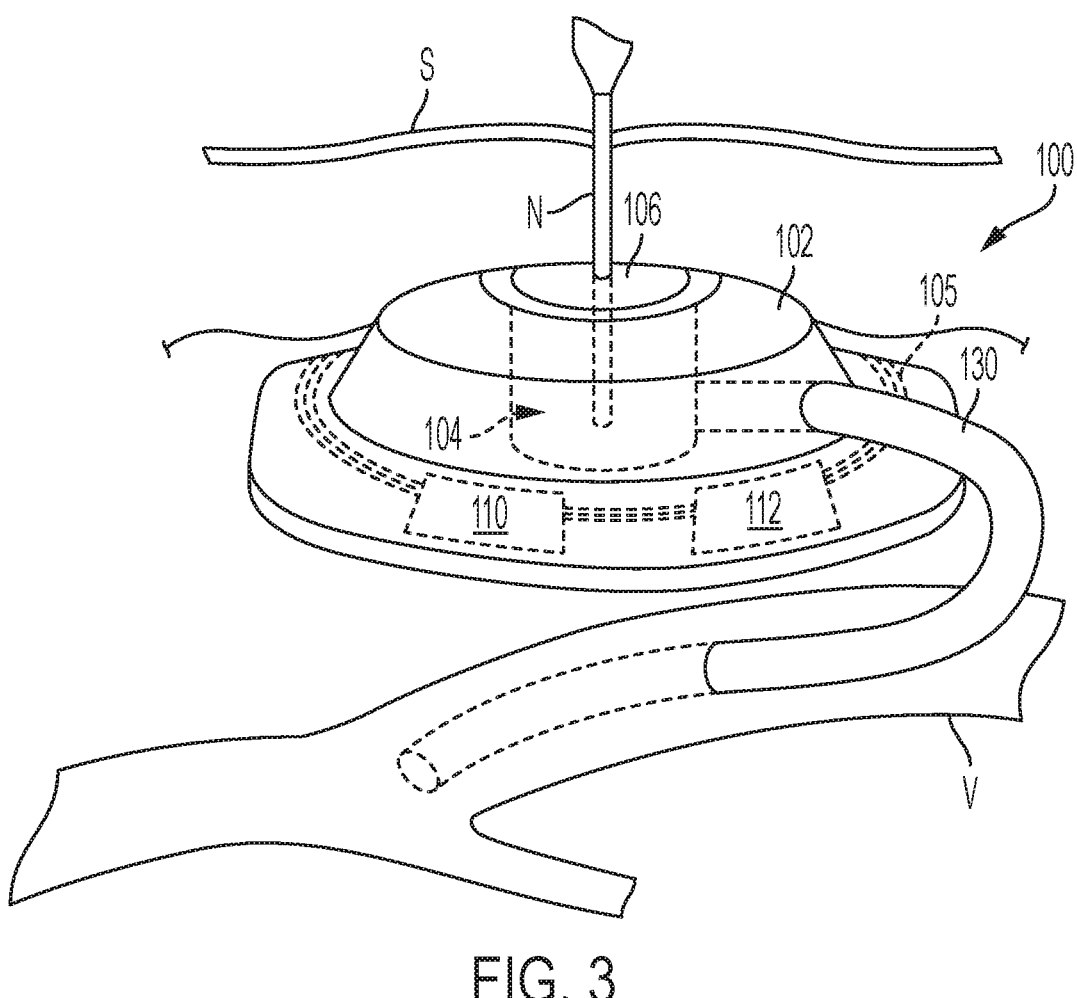
FIG. 3 shows the vascular access device of FIG. 2 implanted within a patient's body.

As shown in FIG. 3, in operation the device 100 is implanted in a patient beneath the skin S, for example in a small pocket created in the upper chest wall just inferior to the clavicle. The catheter 130, which is in fluid communication with the reservoir 104, is inserted into a blood vessel V, for example the internal jugular vein or the subclavian vein with the tip resting in the superior vena cava or the right atrium. A clinician inserts a needle N (e.g., a non-coring or Huber-type needle) through the skin S, through the self-sealing septum 106, and into the fluid reservoir 104. To introduce fluid (e.g., medication) into the patient's blood vessel V, the clinician may advance fluid through the needle N, which then flows through the reservoir 104, the catheter 130, and into the vessel V, or the physician may advance fluid through the needle to fill the reservoir for postponed delivery into the vessel V. To remove fluid from the vessel V (e.g., to aspirate blood from the vessel V for testing), the clinician can apply suction via the needle N, thereby withdrawing fluid (e.g., blood) from the vessel V into the catheter 130, into the fluid reservoir 104, and into the needle N. When the procedure is completed, the clinician removes the needle N, the self-sealing septum 106 resumes a closed configuration, and the device 100 may remain in place beneath the patient's skin S.

Referring again to FIG. 2, as previously mentioned, the device 10 includes a sensing element 110 coupled to the housing 102 and configured to obtain physiological measurements. Although a single sensing element 110 is illustrated for clarity, in various embodiments, the device 100 may include a plurality of sensing elements 110 disposed within or otherwise coupled to the housing 102. In some embodiments, one or more such sensing elements 110 may be disposed on separate structural components that are separated from the housing 102. As used herein, the term "sensing element" may refer to a single sensor or a plurality of discrete, separate sensors.

The device 100 may include at least one controller 112 communicatively coupled to the sensing element 110. The controller 112 may include one or more processors, software components, and memory (not shown). In some examples, the one or more processors include one or more computing components configured to process the physiological measurements received from the sensing element 110 according to instructions stored in the memory. The memory may be a tangible, non-transitory computer-readable medium configured to store instructions executable by the one or more processors. For instance, the memory may be data storage that can be loaded with one or more of the software components executable by the one or more processors to achieve certain functions. In some examples, the functions may involve causing the sensing element 110 to obtain physiological data from the patient. In another example, the functions may involve processing the physiological data to determine one or more physiological parameters and/or provide an indication to the patient and/or clinician of one or more symptoms or medical conditions associated with the determined physiological parameters.

The controller 112 may also include a data communications unit configured to securely transmit data between the device 100 and external computing devices (e.g., local computing device 150, remote computing devices 160 and 170, etc.). In some embodiments, the controller 112 includes a localization unit configured to emit a localization signal (e.g., lights that transilluminate a patient's skin, vibration, a magnetic field, etc.) to aid a clinician in localizing the device 100 when implanted within a patient. The controller 112 can also include a wireless charging unit (such as a coil) configured to recharge a battery (not shown) of the device 100 when in the presence of an interrogation device (e.g., local device 150 or another suitable device).

The system 10 may be configured to continuously and/or periodically obtain physiological measurements via the sensing element 110 in communication with the device 100. The sensing element 110 may be carried by the housing 102 and/or the catheter 130, and/or may include a sensing component separate from the housing 102 and catheter 130 but physically or communicatively coupled to the housing 102 and/or catheter 130. The sensing element 110 may be implanted at the same location as the device 100 or at a different location, or may be positioned on the patient at an exterior location (e.g., on the patient's skin). The sensing element 110 may be permanently coupled to the device 100, or may be configured to temporarily couple to the device 100.

In some embodiments, the sensing element 110 is built into the housing 102 such that only a portion of the sensing element 110 is exposed to the local physiological environment when the device 100 is implanted. For example, the sensing element 110 may comprise one or more electrodes having an external portion positioned at an exterior surface of the housing 102 and an internal portion positioned within the housing 102 and wired to the controller 112. In some embodiments, the sensing element 110 may comprise one or more electrodes having an internal portion positioned at an interior surface of the housing 102 at the interface with the port reservoir 104 or junction of the reservoir 104 and the catheter 130, or extending into the catheter 130.

In some embodiments the sensing element 110 may be completely contained within the housing 102. For example, the sensing element 110 may comprise one or more pulse oximeters enclosed by the housing 102 and positioned adjacent a window in the housing 102 through which light emitted from the pulse oximeter may pass to an external location, and back through which light reflected from the external location may pass for detection by a photodiode of the pulse oximeter. In such embodiments the window may be, for example, a sapphire window that is brazed into place within an exterior wall of the housing 102.

The sensing element 110 may comprise at least one sensor completely enclosed by the housing 102 and at least one sensor that is partially or completely positioned at an external location, whether directly on the housing 102 and/or catheter 130 or separated from the housing 102 and/or catheter 130 (but still physically coupled to the housing 102 and/or catheter 130 via a wired connection, for example). In some embodiments, at least a portion of the sensing element 110 is positioned at and/or exposed to an interior region of the reservoir 104.

In some embodiments, the sensing element 110 may include a separate controller (not shown) that comprises one or more processors and/or software components. In such embodiments, the sensing element 110 may process at least some of the physiological measurements to determine one or more physiological parameters, and then transmit those physiological parameters to the controller 112 of the device 100 (with or without the underlying physiological data). In some examples, the sensing element 110 may only partially process at least some of the physiological measurements before transmitting the data to the controller 112. In such embodiments, the controller 112 may further process the received physiological data to determine one or more physiological parameters. The local computing device 150 and/or the remote computing devices 160, 170 may also process some or all of the physiological measurements obtained by the sensing element 110 and/or physiological parameters determined by the sensing element 110 and/or the controller 112.

According to some aspects of the technology, the sensing element 110 may include memory. The memory may be a non-transitory computer-readable medium configured to permanently and/or temporarily store the physiological measurements obtained by the sensing element 110. In those embodiments where the sensing element 110 includes its own processor(s), the memory may be a tangible, non-transitory computer-readable medium configured to store instructions executable by the processor(s).

In some embodiments, the sensing element(s) 110 and/or controller 112 may identify, monitor, and communicate patient information by electromagnetic, acoustic, motion, optical, thermal, or biochemical sensing elements or means. The sensing element(s) 110 may include, for example, one or more temperature sensing elements (e.g., one or more thermocouples, one or more digital temperature sensors, one or more thermistors or other type of resistance temperature detector, etc.), one or more impedance sensing elements (e.g., one or more electrodes), one or more pressure sensing elements, one or more optical sensing elements, one or more flow sensing elements (e.g., a Doppler velocity sensing element, an ultrasonic flow meter, etc.), one or more ultrasonic sensing elements, one or more pulse oximeters, one or more chemical sensing elements, one or more movement sensing elements (e.g., one or more accelerometers), one or more pH sensing elements, an electrocardiogram ("ECG" or "EKG") unit, one or more electrochemical sensing elements, one or more hemodynamic sensing elements, and/or other suitable sensing devices.

The sensing element 110 may comprise one or more electromagnetic sensing elements configured to measure and/or detect, for example, impedance, voltage, current, or magnetic field sensing capability with a wire, wires, wire bundle, magnetic node, and/or array of nodes. The sensing element 110 may comprise one or more acoustic sensing elements configured to measure and/or detect, for example, sound frequency, within human auditory range or below or above frequencies of human auditory range, beat or pulse pattern, tonal pitch melody, and/or song. The sensing element 110 may comprise one or more motion sensing elements configured to measure and/or detect, for example, vibration, movement pulse, pattern or rhythm of movement, intensity of movement, and/or speed of movement. Motion communication may occur by a recognizable response to a signal. This response may be by vibration, pulse, movement pattern, direction, acceleration, or rate of movement. Motion communication may also be by lack of response, in which case a physical signal, vibration, or bump to the environment yields a motion response in the surrounding tissue that can be distinguished from the motion response of the sensing element 110. Motion communication may also be by characteristic input signal and responding resonance. The sensing element 110 may comprise one or more optical sensing elements which may include, for example, illuminating light wavelength, light intensity, on/off light pulse frequency, on/off light pulse pattern, passive glow or active glow when illuminated with special light such as UV or "black light", or display of recognizable shapes or characters. It also includes characterization by spectroscopy, interferometry, response to infrared illumination, and/or optical coherence tomography. The sensing element 110 may comprise one or more thermal sensing elements configured to measure and/or detect, for example, device 100 temperature relative to surrounding environment, the temperature of the device 100 (or portion thereof), the temperature of the environment surrounding the device 100 and/or sensing element 110, or differential rate of the device temperature change relative to surroundings when the device environment is heated or cooled by external means. The sensing element 110 may comprise one or more biochemical devices which may include, for example, the use of a catheter, a tubule, wicking paper, or wicking fiber to enable micro-fluidic transport of bodily fluid for sensing of protein, RNA, DNA, antigen, and/or virus with a micro-array chip.

In some aspects of the technology, the controller 112 and/or sensing element 110 may be configured to detect and/or measure the concentration of blood constituents, such as sodium, potassium, chloride, bicarbonate, creatinine, blood urea nitrogen, calcium, magnesium, and phosphorus. The system 10 and/or the sensing element 110 may be configured to evaluate liver function (e.g., by evaluation and/or detection of AST, ALT, alkaline phosphatase, gamma glutamyl transferase, troponin, etc.), heart function (e.g., by evaluation and/or detection of troponin), coagulation (e.g., via determination of prothrombin time (PT), partial thromboplastin time (PTT), and international normalized ratio (INR)), and/or blood counts (e.g., hemoglobin or hematocrit, white blood cell levels with differential, and platelets). In some embodiments, the system 10 and/or the sensing element 110 may be configured to detect and/or measure circulating tumor cells, circulating tumor DNA, circulating RNA, multigene sequencing of germ line or tumor DNA, markers of inflammation such as cytokines, C reactive protein, erythrocyte sedimentation rate, tumor markers (PSA, beta-HCG, AFP, LDH, CA 125, CA 19-9, CEA, etc.), and others.

As previously mentioned, the system 10 may determine one or more physiological parameters based on the physiological measurements and/or one or more other physiological parameter(s). For example, the system 10 may be configured to determine physiological parameters such as heart rate, temperature, blood pressure (e.g., systolic blood pressure, diastolic blood pressure, mean blood pressure), blood flow rate, blood velocity, pulse wave speed, volumetric flow rate, reflected pressure wave amplitude, augmentation index, flow reserve, resistance reserve, resistive index, capacitance reserve, hematocrit, heart rhythm, electrocardiogram (ECG) tracings, body fat percentage, activity level, body movement, falls, gait analysis, seizure activity, blood glucose levels, drug/medication levels, blood gas constituents and blood gas levels (e.g., oxygen, carbon dioxide, etc.), lactate levels, hormone levels (such as cortisol, thyroid hormone (T4, T3, free T4, free T3), TSH, ACTH, parathyroid hormone), and/or any correlates and/or derivatives of the foregoing measurements and parameters (e.g., raw data values, including voltages and/or other directly measured values). In some embodiments, one or more of the physiological measurements can be utilized or characterized as a physiological parameter without any additional processing by the system 10.

The system 10 may also determine and/or monitor derivatives of any of the foregoing physiological parameters (also referred to herein as "physiological parameters"), such as a rate of change of a particular parameter, a change in a particular parameter over a particular time frame, etc. As but a few examples, the system 10 may be configured to determine as temperature over a specified time, a maximum temperature, a maximum average temperature, a minimum temperature, a temperature at a predetermined or calculated time relative to a predetermined or calculated temperature, an average temperature over a specified time, a maximum blood flow, a minimum blood flow, a blood flow at a predetermined or calculated time relative to a predetermined or calculated blood flow, an average blood flow over time, a maximum impedance, a minimum impedance, an impedance at a predetermined or calculated time relative to a predetermined or calculated impedance, a change in impedance over a specified time, a change in impedance relative to a change in temperature over a specified time, a change in heart rate over time, a change in respiratory rate over time, activity level over a specified time and/or at a specified time of day, and other suitable derivatives.

Measurements may be obtained continuously or periodically at one or more predetermined times, ranges of times, calculated times, and/or times when or relative to when a measured event occurs. Likewise, physiological parameters may be determined continuously or periodically at one or more predetermined times, ranges of times, calculated times, and/or times when or relative to when a measured event occurs.

Based on the determined physiological parameters, the system 10 of the present technology is configured to provide an indication of the patient's health to the patient and/or a clinician. For example, the controller 112 may compare one or more of the physiological parameters to a predetermined threshold or range and, based on the comparison, provide an indication of the patient's health. For instance, if the determined physiological parameter(s) is above or below the predetermined threshold or outside of the predetermined range, the system 10 may provide an indication that the patient is at risk of, or has already developed, a medical condition characterized by symptoms associated with the determined physiological parameters. As used herein, a "predetermined range" refers to a set range of values, and "outside of a/the predetermined range" refers to (a) a measured or calculated range of values that only partially overlap the predetermined range or do not overlap any portion of a predetermined range of values. As used herein, a "predetermined threshold" refers to a single value or range of values, and a parameter that is "outside" of "a predetermined threshold" refers to a situation where the parameter is (a) a measured or calculated value that exceeds or fails to meet a predetermined value, (b) a measured or calculated value that falls outside of a predetermined range of values, (c) a measured or calculated range of values that only partially overlaps a predetermined range of values or does not overlap any portion of a predetermined range of values, or (d) a measured or calculated range of values where none of the values overlap with a predetermined value.

Predetermined parameter thresholds and/or ranges can be empirically determined to create a look-up table. Look-up table values can be empirically determined, for example, based on clinical studies and/or known healthy or normal values or ranges of values. The predetermined threshold may additionally or alternatively be based on a particular patient's baseline physiological parameters.

Medical conditions detected and/or indicated by the system 10 may include, for example, sepsis, pulmonary embolism, metastatic spinal cord compression, anemia, dehydration/volume depletion, vomiting, pneumonia, congestive heart failure, performance status, arrythmia, neutropenic fever, acute myocardial infarction, pain, opioid toxicity, nicotine or other drug addiction or dependency, hyperglycemic/diabetic ketoacidosis, hypoglycemia, hyperkalemia, hypercalcemia, hyponatremia, one or more brain metastases, superior vena cava syndrome, gastrointestinal hemorrhage, immunotherapy-induced or radiation pneumonitis, immunotherapy-induced colitis, diarrhea, cerebrovascular accident, stroke, pathological fracture, hemoptysis, hematemesis, medication-induced QT prolongation, heart block, tumor lysis syndrome, sickle cell anemia crisis, gastroparesis/cyclic vomiting syndrome, hemophilia, cystic fibrosis, chronic pain, and/or seizure. Any of the systems and/or devices disclosed herein (such as devices 4A-19B) may be used to monitor a patient for any of the foregoing medical conditions.

For the purposes of this specification and appended claims, unless otherwise indicated, all numbers expressing temperatures, percentage changes in physiological parameters, concentration of blood constituents, heart rate, respiratory rate, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a sensing element" includes one, two, three or more sensing elements.

As used herein, the term "at least one of A, B, and C" means any of A, B, or C individually, as well as any combination of two or more of A, B, and C. For example, "at least one of A, B, and C" includes A, B, C, AB, AC, BC, and ABC.

Selected Examples of Vascular Access Devices

FIGS. 4A-20B illustrate various example configurations of vascular access devices having physiological sensors and/or other electronic elements. The vascular access devices 400 can include some or all of the features of vascular access device 100 described above with respect to FIGS. 1-3. In many of the following examples, the vascular access device 400 includes an outer housing 402 that defines or encloses a reservoir component 404, an electronics component 406, a battery component 408, and a coil component 410. The housing 402 can therefore retain the various elements the device 400 together. The housing 402 can be made of a biocompatible material such as metal (e.g., titanium), ceramic, polymer (e.g., PEEK, silicone), or other biocompatible materials. In some embodiments, the exterior housing 402 can be flexible, thereby increasing patient comfort when implanted and improving conformity with the adjacent anatomy. In some embodiments, the housing 402 can hermetically seal some or all of the interior elements of the device 400. As described in more detail, these components (or elements of these components) may be arranged in different geometric and electrical configurations. In some embodiments, this can result in devices having a lower profile, a smaller footprint, more mechanical flexibility, and/or more modularity allowing for variation of components in manufacturing. Additionally, the shape, arrangement, and configuration of certain components can improve usability for a clinician and/or increase patient comfort.

The reservoir component 404 can include a body 405 (which can be a portion of the housing 402) that defines an interior chamber 412 (FIG. 5B) to receive fluid therein. A self-sealing septum 414 or other cover may enclose the chamber 412 and define an access path through which a needle may be inserted. The septum 414 can be, for example, a membrane made of silicone or other deformable, self-sealing, biocompatible material. The reservoir component 404 also includes an outlet port 416 configured to be mated to a catheter. For example, the outlet port 416 can be defined by a portion of the housing 402 having a barbed connection or other suitable mechanical connection for removably receiving a catheter thereon. In use, a needle can be removably inserted into the chamber 412 through the septum 414, and a catheter can be fluidically coupled to the outlet port 416, thereby establishing a fluid path between the needle and the catheter for introduction of fluid (e.g., medication) or withdrawal of fluid (e.g., aspiration of blood for testing).

In various embodiments, the vascular access device 400 can have a longest length of between about 10 mm to about 100 mm, between about 20 mm to about 80 mm, between about 30 mm to about 70 mm, between about 40 mm to about 60 mm, or about 50 mm. In various embodiments, the vascular access device 400 can have a width as measured substantially orthogonal to its length of between about 5 mm to about 40 mm, between about 10 mm to about 30 mm, or about 25 mm. In some embodiments, the vascular access device 400 can have a height of between about 5 mm to about 50 mm, between about 10 mm and about 30 mm, or about 15 mm. In various embodiments, the septum of the vascular access device can have a diameter of between about 3 mm to about 15 mm, between about 5 mm to about 12 mm, or about 10 mm. In various embodiments, the septum of the vascular access device can have a thickness of between about 2 mm to about 10 mm, between about 3 mm to about 8 mm, between about 4 mm to about 6 mm, or about 5 mm. In various embodiments, the reservoir component 404 of the vascular access device 400 may include a funnel portion that defines a needle access path through the septum 414 at an angle with respect to a planar bottom surface of the device, for example at an angle of between about 0 degrees to about 45 degrees, between about 10 degrees to about 30 degrees, or about 25 degrees. In other embodiments, the septum 414 of the reservoir component 404 may be disposed over a top surface such that an access path for the needle may be substantially orthogonal to a plane of the bottom surface of the device 400.

In some embodiments, the battery component 408 includes a rechargeable or a non-rechargeable battery configured to provide power to the electronic components. Example batteries include lithium ion, magnesium ion, nickel cadmium, nickel metal hydride, or any other suitable battery configured to power the onboard electrical components of the vascular access device. The battery can assume a wide variety of form factors, for example disc-shaped, cylindrical, annular, irregular, or other shape. In some embodiments, the battery can be a coin-shaped battery having a diameter of between about 10-30 mm, though other sizes are also possible. The battery component 408 can be enclosed within the housing 402 at various positions with respect to the other components of the device 400, as described in more detail below.

The electronics component 406 can include, for example a printed circuit board (flexible, rigid, or semi-rigid) or other suitable substrate that supports one or more electronic elements, such as sensing element(s) 418, memory, one or more controllers (e.g., a central processing unit, digital signal processor, application-specific integrated circuit, or any other logic processing unit), wireless communication elements (e.g., wireless communication chip, antennae, etc.), wireless power receivers, and any other suitable electronic elements (e.g., filters, analog-to-digital converters, etc.). In some embodiments, the electronics component 406 can be distributed about the device 400, such that a first portion of the electronics component 406 (e.g., processor, memory, wireless communications chip, etc.) is positioned in a first region of the device 400 and another portion of the electronics component 406 (e.g., the sensing elements 418) is positioned in a second region of the device 400. In some embodiments, the battery component 408 and the electronics component 406 can be combined, co-mounted, or otherwise arranged together as a single unit. In other embodiments, the battery component 408 and the electronics component 406 can be separated from one another and connected only via electrical leads and various elements of the electronics component 406 can be separated from one another and connected only via electrical leads.

In some embodiments, the battery component 408 and/or at least a portion of the electronics component 406 are enclosed within an encasement 409, which can be disposed entirely within the outer housing 402. The encasement 409 can include one or more openings allowing conductive leads to extend between the battery component 408 or portions of the electronics component 406 and any elements exterior to the encasement 409, such as sensing elements 418, the coil component 410, etc. In some embodiments, the encasement 409 can be metallic (e.g., titanium), plastic, medical grade silicone, ceramic, or other suitable material. In some embodiments, the encasement 409 provides a biocompatible hermetic seal to protect the interior components (e.g., battery component 408 and/or electronics component 406) therein.

The sensing elements 418 of the electronics component are configured to obtain one or more physiological measurements while implanted within the body. In some embodiments, the sensing elements 418 can include any of the sensing elements 110 described above with respect to FIGS. 1-3. The sensing elements 418 can be configured to obtain any number of different physiological measurements and/or one or more other physiological parameters, such as any of those disclosed in U.S. patent application Ser. No. 16/197,083, filed Nov. 20, 2018, which is hereby incorporated by reference in its entirety. The sensing elements 418 can include temperature sensors, pulse oximeters, accelerometers, EKG sensors, magnetometers, pH sensors, and other suitable sensors. These or other such sensors may be configured to determine physiological parameters such as body temperature, heart rate, temperature, blood pressure (e.g., systolic blood pressure, diastolic blood pressure, mean blood pressure), blood flow rate, blood velocity, pulse wave speed, volumetric flow rate, reflected pressure wave amplitude, augmentation index, flow reserve, resistance reserve, resistive index, capacitance reserve, hematocrit, heart rhythm, electrocardiogram (ECG) tracings, body fat percentage, activity level, body movement, falls, gait analysis, seizure activity, blood glucose levels, drug/medication levels, blood gas constituents and blood gas levels (e.g., oxygen, carbon dioxide, etc.), lactate levels, hormone levels (such as cortisol, thyroid hormone (T4, T3, free T4, free T3), TSH, ACTH, parathyroid hormone), and/or any correlates and/or derivatives of the foregoing measurements and parameters (e.g., raw data values, including voltages and/or other directly measured values). Additional details can be found in U.S. patent application Ser. No. 16/197,083, filed Nov. 20, 2018, which is hereby incorporated by reference in its entirety. regarding obtaining physiological measurements via the sensing elements 418, determining one or more physiological parameters, and providing an indication of a medical condition based on determining the one or more physiological parameters.

In some embodiments, the electronics component 406 of the vascular access device 400 can include a localization unit. Such a localization unit can include an emitter configured to emit a localization signal in addition to a controller (e.g., controller 112 (FIG. 1), a central processing unit, digital signal processor, application-specific integrated circuit, or any other logic processing unit) that reads instructions from the memory to perform suitable operations. The localization unit can be configured to emit one or more localization signals from the vascular access device 400 to aid a clinician in identifying the location of the device when implanted within a patient. In one example, the localization unit can include one or more light sources disposed about the device, and the localization signal can include the emission of light from the light sources. The emitted light can be configured to transilluminate the skin to indicate a location of the implantable device to a clinician. In this instance, the localization reader can include a light sensor or array of sensors configured to identify the lights transilluminating the patient's skin. In further examples, the localization signal may include emitted sound, a signature magnetic field generated by one or more magnets, emitted RF signals, radiation from a decaying radioisotope, ultrasound, vibration, protrusions raised from a surface of the device, increased temperature from a heating element, etc. Additional details regarding emission of localization signals via the electronics component 406 can be found in U.S. Provisional Patent Application No. 62/769,698, filed Nov. 20, 2018, which is hereby incorporated by reference in its entirety.

The electronics component 406 of the vascular access device 400 can also include a data communications unit that is configured to communicate wirelessly with a paired device. The data communications unit can include, for example, a wireless communications chip (e.g., a Bluetooth Low Energy chip), a wireless antenna, or other suitable wireless communications elements. Communication between the data communications unit and a paired device can be mediated by, for example, near-field communication (NFC), infrared wireless, Bluetooth, ZigBee, Wi-Fi, inductive coupling, capacitive coupling, or any other suitable wireless communication link. The data communications unit may transmit data including, for example, physiological measurements obtained via the sensing elements, patient medical records, device performance metrics (e.g., battery level, error logs, etc.), or any other such data stored by the vascular access device 400. Additional details regarding data communication via the electronics component 406 can be found in U.S. Provisional Patent Application No. 62/769, 698, filed Nov. 20, 2018, which is hereby incorporated by reference in its entirety.

The coil component 410 of the vascular access device 400 can include a length of conductive material such as copper wire wrapped sequentially into a circular, elliptical, square, or other shape. The coil component 410 can be in electrical communication with the battery component 408 and the electronics component 406, for example via conductive leads or other suitable connections. In some embodiments, the coil component 410 is configured to receive an induced electrical current in the presence of a charging coil positioned in proximity to the coil component. For example, when the vascular access device 400 is implanted within a patient, and a charging coil is positioned over the patient's skin adjacent to the implanted device 400, alternating current driven through the charging coil creates an alternating magnetic field that, in turn, induces an electrical current in the coil component 410 of the vascular access device 400. This induced current in the coil component 410 can be used to recharge the battery component 408 and/or to power other elements of the electronics component 406 to perform other operations, such as data transmission, emission of localization signals, etc. In some embodiments, the electronics component 406 includes a wireless power receiver configured to harvest electrical energy from the coil component 410 and recharge the battery component 408. Additional details regarding wireless charging via the coil component 410 can be found in U.S. Provisional Patent Application No. 62/769,698, filed Nov. 20, 2018, which is hereby incorporated by reference in its entirety.

Figure 4A:
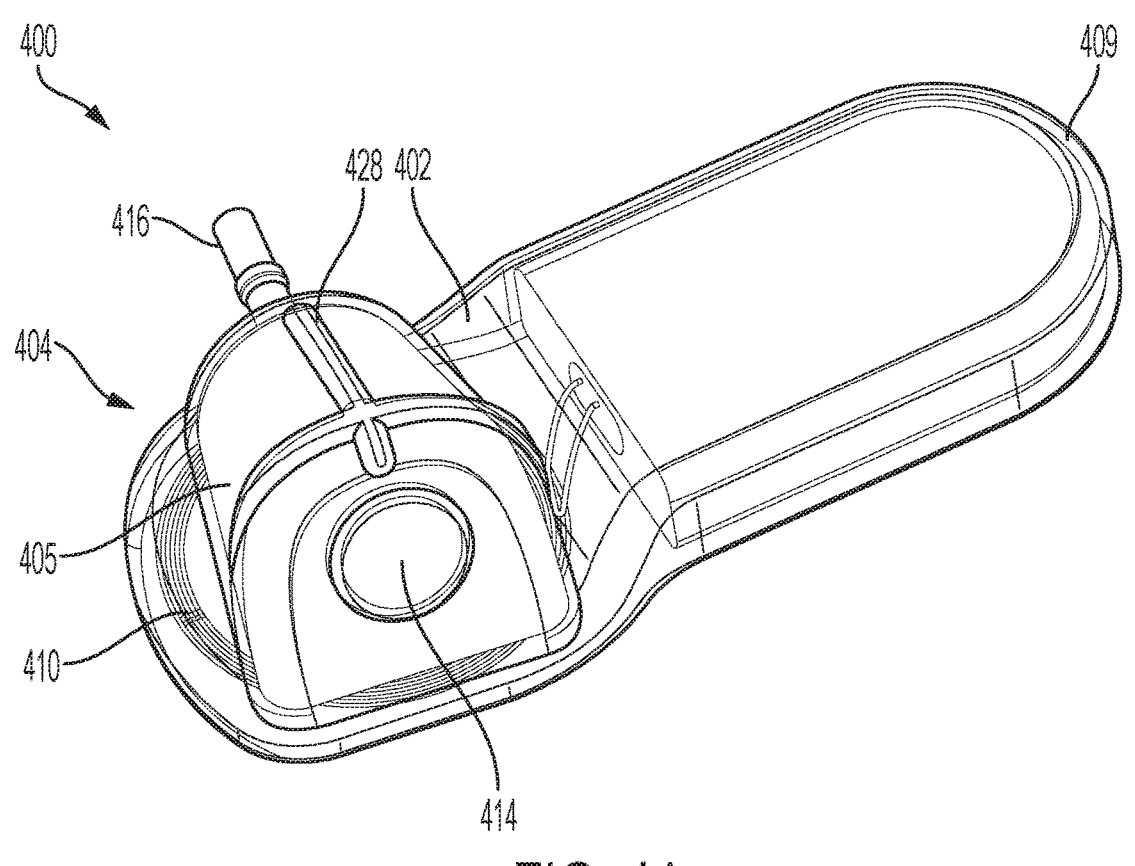
FIG. 4A is a top perspective view of a vascular access device in accordance with the present technology.
Figure 4B:
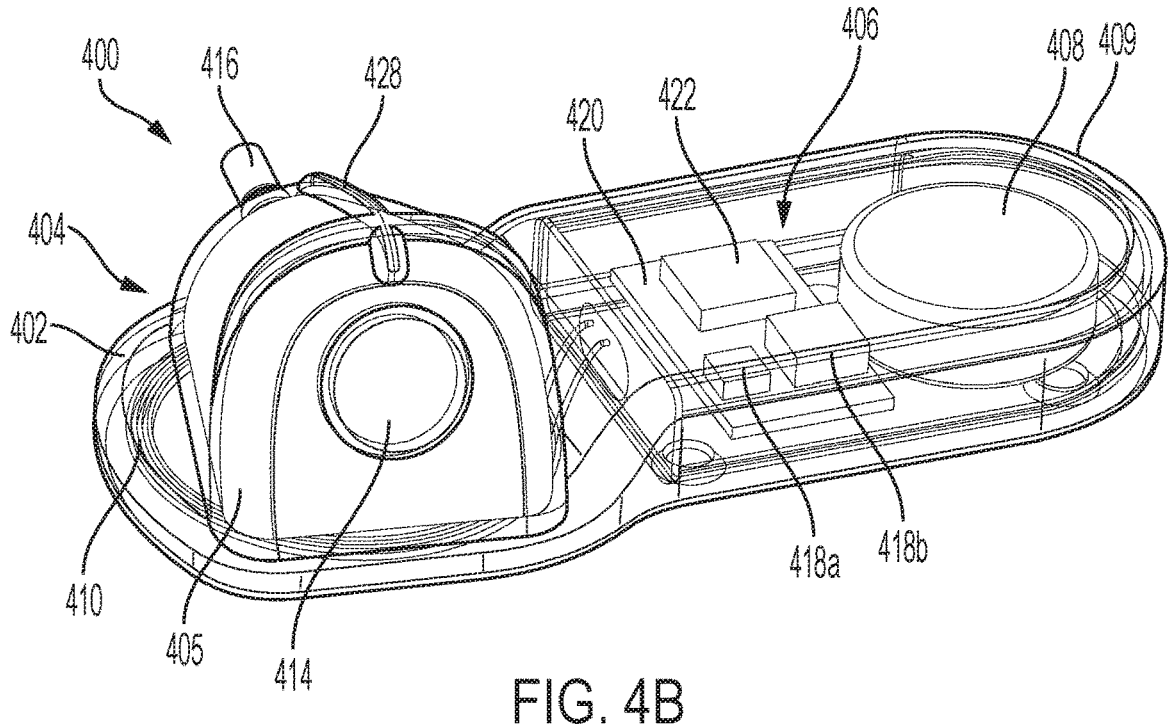
FIG. 4B is a top perspective view of the vascular access device of FIG. 4A with the encasement shown transparently.
Figure 4C:
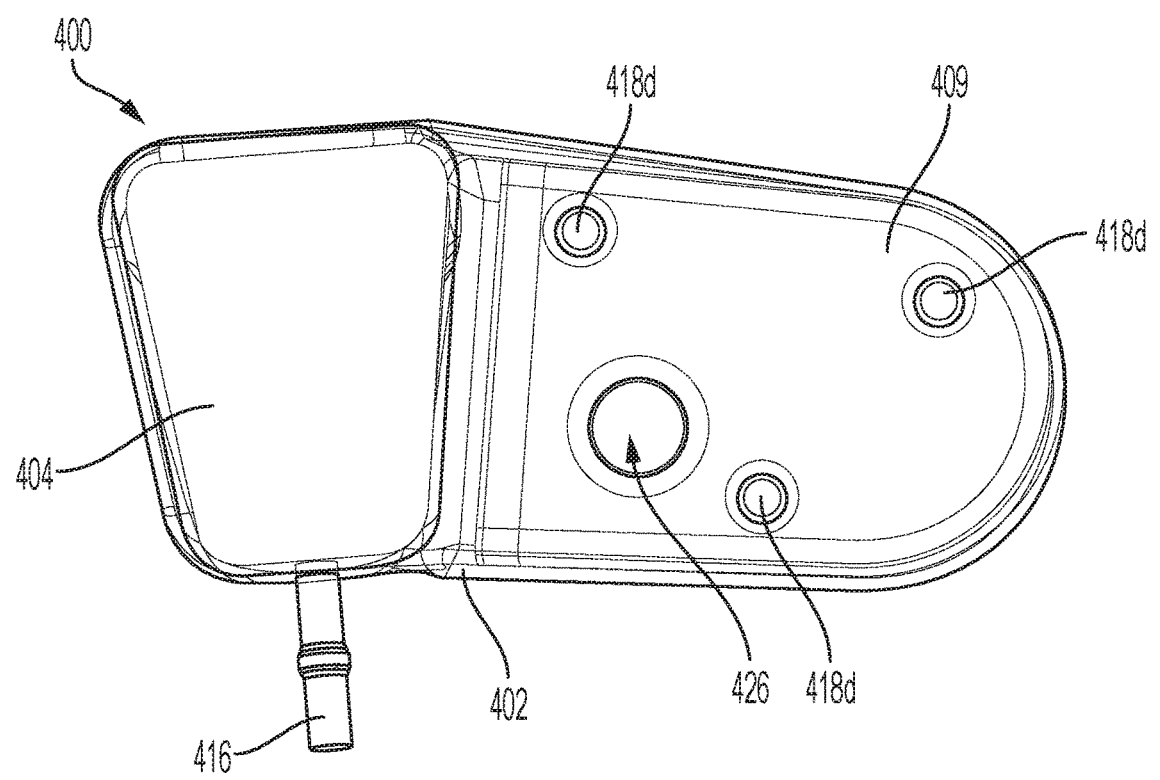
FIG. 4C is a bottom view of the vascular access device of FIGS. 4A and 4B.
Figure 4D:
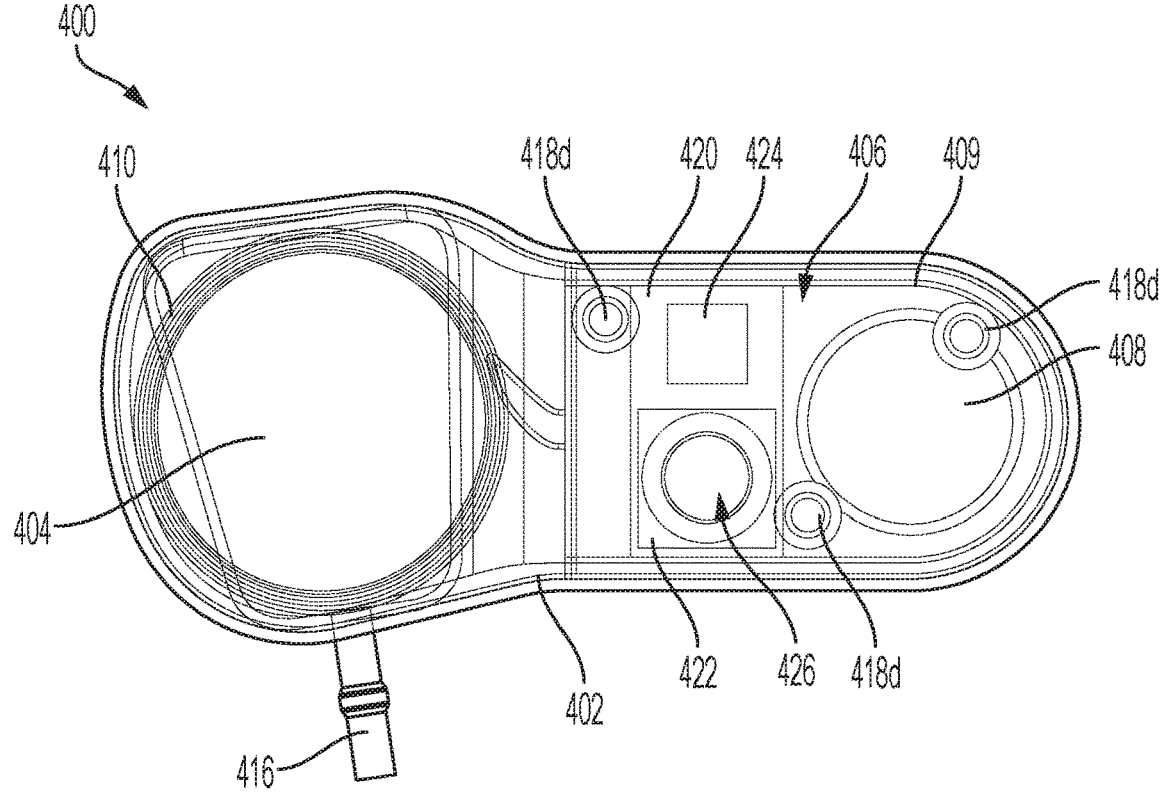
FIG. 4D is a bottom view of the vascular access device of FIGS. 4A-4C with the encasement shown transparently.
Figure 5A:
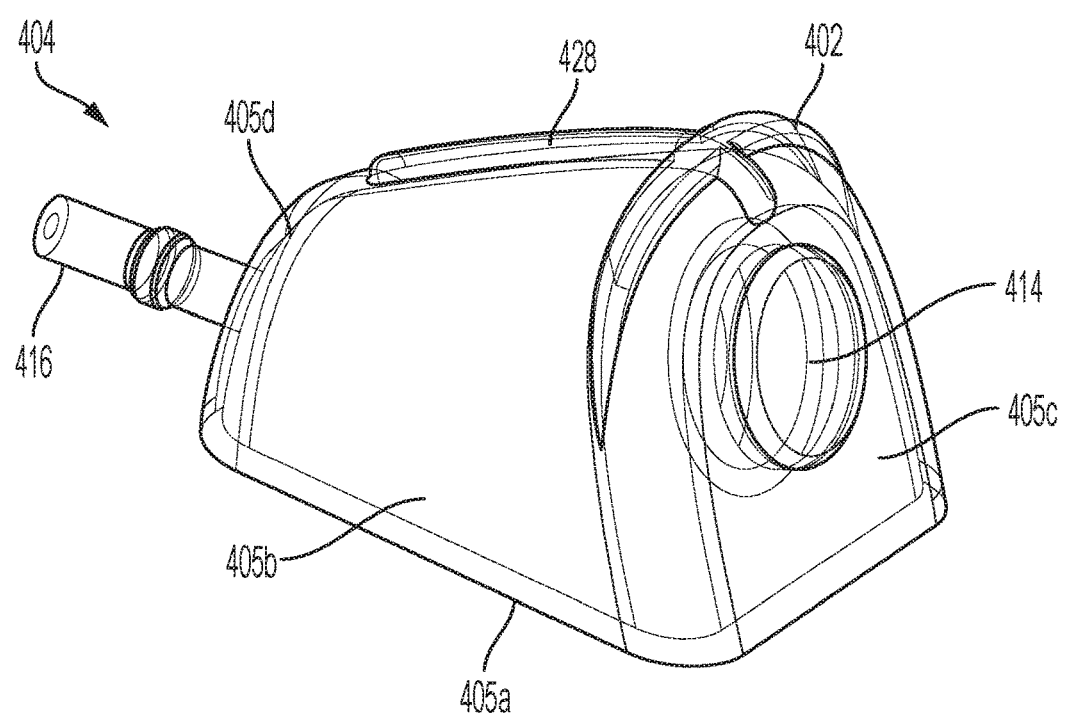
FIGS. 5A and 5B are top perspective and side cross-sectional views, respectively, of the reservoir component of the vascular access device shown in FIGS. 4A-4D.
Figure 5B:
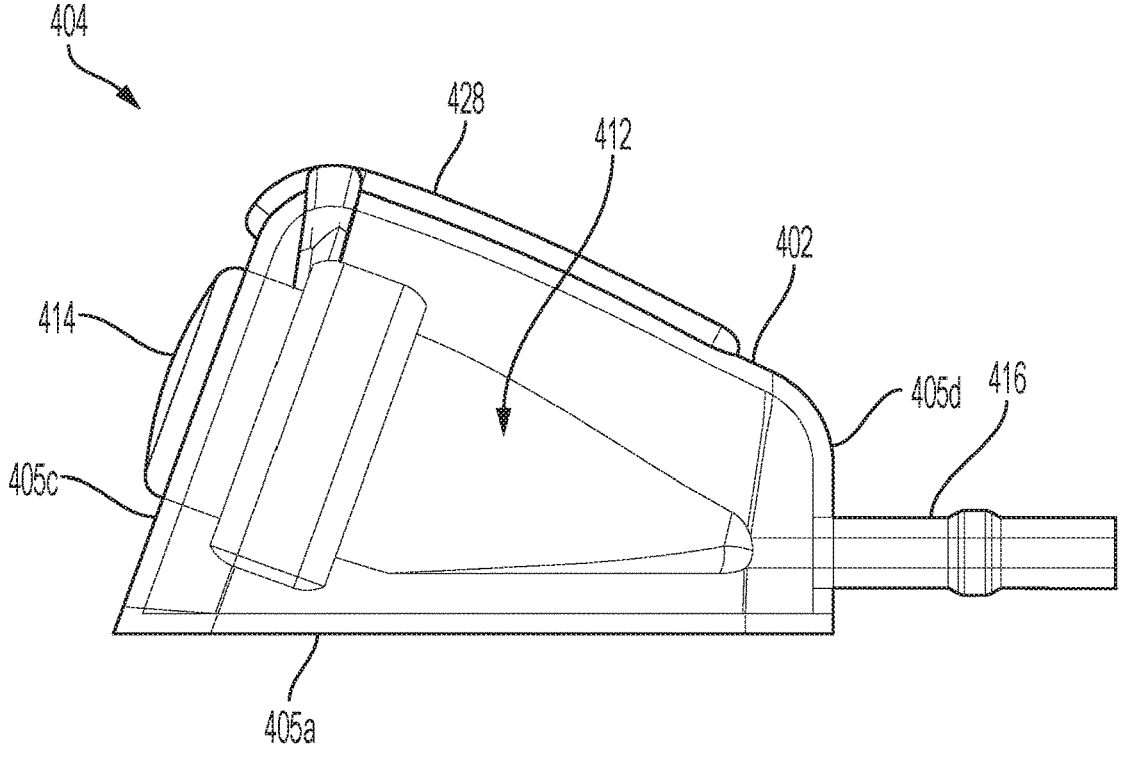

FIGS. 4A-4D are top perspective and bottom views of an example vascular access device 400. The housing 402 is shown transparently in each of these drawings, and the encasement 409 shown transparently in FIGS. 4B and 4C for clarity. FIGS. 5A and 5B are top perspective and side cross-sectional views, respectively, of the reservoir component 404 of the vascular access device 400 shown in FIGS. 4A and 4B. Referring to FIGS. 4A-5 together, the electronics component 406 and the battery component 408 are mounted together in a first region of the device 400 within the encasement 409 while the coil component 410 and the reservoir component 404 are mounted in a second region that is laterally displaced from the first region. As illustrated, the coil component 410 is disposed beneath the body 405 of the reservoir component 404 and is electrically coupled to the battery component 408 and/or the electronics component 406 via conductive leads.

In this embodiment, the battery component 408 is substantially cylindrical. As best seen in FIGS. 4B and 4D, the electronics component 406 can include a plurality of individual elements mounted to one or both sides of a printed circuit board 420. These include a wireless communication module 422 (e.g., a Bluetooth Low Energy chip or similar module configured to enable short-range or long-range wireless communication between the device 400 and one or more remote computing devices), a wireless charging module 424 (e.g., a wireless power receiver chip), and a plurality of sensing elements 418a-d (collectively "sensing elements 418"). These sensing elements can include an accelerometer 418a, a temperature sensor 418b, a pulse oximeter 418c, and a plurality of EKG electrodes 418d. The device 400 can include a window 426 disposed in the lower portion of the encasement 409 and/or the housing 402 and substantially aligned with the pulse oximeter 418c, such that optical signals can be transmitted between the pulse oximeter 418c and adjacent tissue or fluids when the device 400 is implanted within the body. The window 426 can be transparent or translucent, for example being made of sapphire, reinforced glass, or other suitable material that allows transmission of optical signals therethrough. The EKG electrodes 418d can be coupled to the housing 402 and exposed to the exterior of the device 400 so as to be in contact with tissue or fluids when implanted within the body. The EKG electrodes 418d can be electrically coupled to a processing unit or other suitable module for receiving, processing, and storing measurements from the EKG electrodes.

As noted previously, in some embodiments the electronics component 406 can include additional or different sensing elements 418. For example, the sensing elements 418 can include, for example, one or more temperature sensing elements (e.g., one or more thermocouples, one or more thermistors, a digital temperature sensor with integrated memory, etc.), one or more impedance sensing elements (e.g., one or more electrodes), one or more pressure sensing elements, one or more optical sensing elements, one or more flow sensing elements (e.g., a Doppler velocity sensing element, an ultrasonic flow meter, etc.), one or more ultrasonic sensing elements, one or more pulse oximeters, one or more chemical sensing elements, one or more movement sensing elements (e.g., one or more accelerometers), one or more pH sensing elements, an electrocardiogram ("ECG") unit, one or more electrochemical sensing elements, one or more hemodynamic sensing elements, and/or other suitable sensing devices. The sensing elements 418 can be configured to detect a variety of physiological parameters in different embodiments as described previously.

As best seen in FIGS. 5A and 5B, the reservoir component 404 has a body 405 with a substantially planar bottom surface 405a and a curved upper surface 405b. The septum 414 is disposed at a first end surface 405c that is substantially vertically oriented with respect to the bottom surface 405a. The outlet port 416 extends away from a second end surface 405d that is opposite the first end surface 405c. The curved upper surface 405b defines a sloped portion in which a height of the body 405 is higher at the first end surface 405c than at the second end surface 405d. The first end surface on which the septum 414 is positioned can be oriented non-orthogonally with respect to the bottom surface 405a, such that the first end surface 405c tapers inwardly as it extends up away from the bottom surface 405a of the reservoir component 404.

The septum 414 can assume a generally circular shape and be disposed within an aperture defined by the body 405 and the exterior housing 402. In some embodiments, the diameter of the septum can be between about 5 and about 20 mm, for example approximately 10 mm. The position and orientation of the septum 414 is such that, when the device 400 is implanted within a patient (and the upper surface 405b is positioned nearest the patient's skin), the axis of insertion of a needle into the septum 414 is acutely angled with respect to a patient's skin, and may resemble an angle of insertion for a standard IV needle as is familiar to clinicians. On the upper surface of the reservoir component 404 is a longitudinal ridge 428. In some embodiments, this ridge 428 may provide a protruding surface that can be detected via palpation. As the ridge is axially aligned with the septum 414, locating the ridge via palpation or other means can help guide a clinician when inserting a needle through the septum 414.

FIGS. 6-19B illustrate additional example vascular access devices 400. These example devices can have some or all of the components described above with respect to FIGS. 4A-5, and may omit any feature or combination of features of the device described above with respect to FIGS. 4A-5. For example, in some of the following examples, the device does not include a coil component 410. Similarly, in some examples, more or fewer sensing elements 418 are included in the device 400. Additionally, in these and other examples, the configuration, relative positioning, sizing, and arrangement of the various components may vary. For example, in some embodiments the battery component 408 may be stacked or otherwise vertically aligned with at least a portion of the electronics component 406, while in other embodiments the battery component 408 may be positioned laterally adjacent to the electronics component 406.

Figure 6:
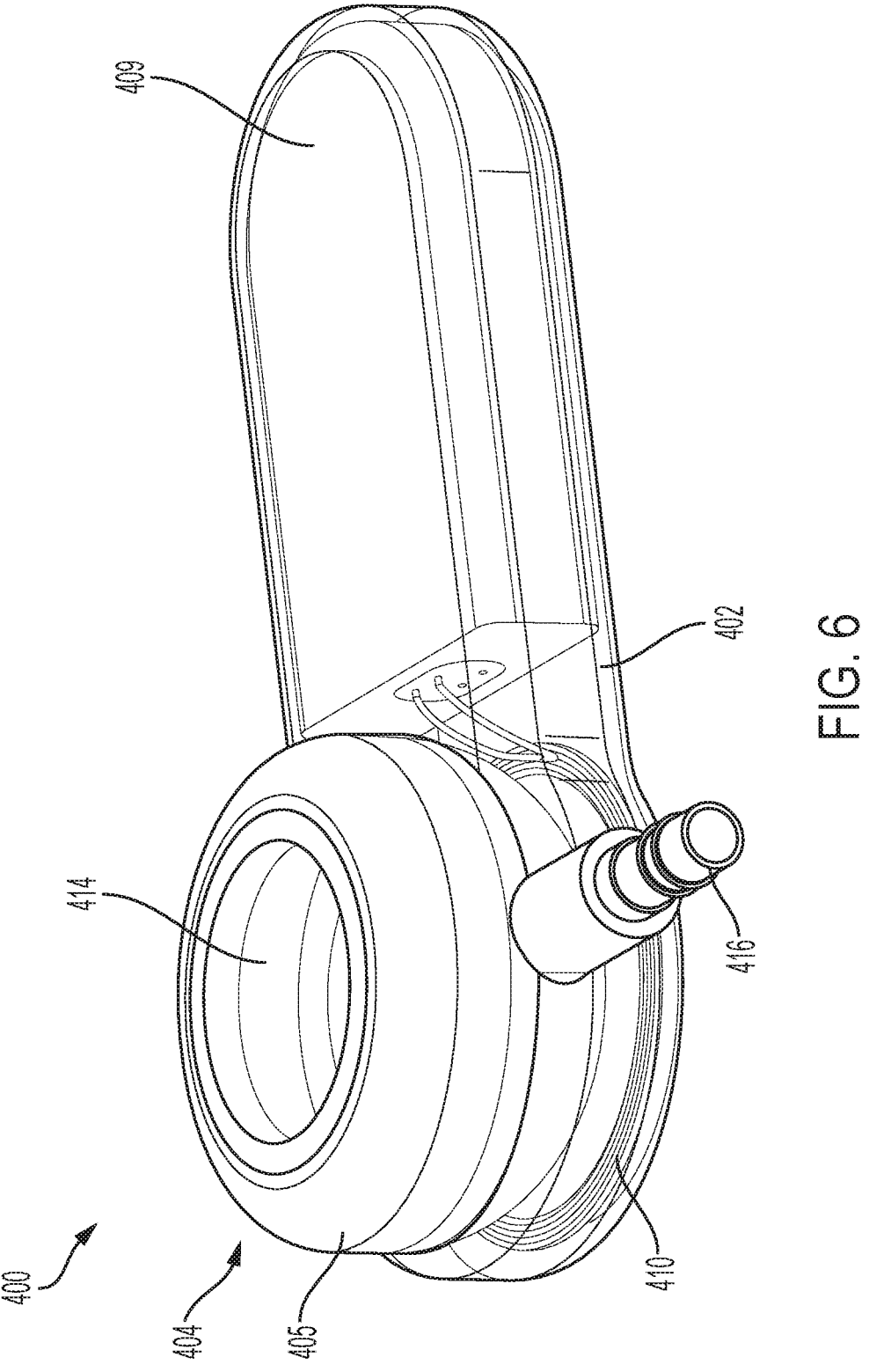
FIG. 6 illustrates another example vascular access device in accordance with the present technology.

FIG. 6 illustrates another example vascular access device 400. In the illustrated embodiment, the electronics component 406, battery component 408, and/or the coil component 410 can be substantially similar to those described above with respect to FIGS. 4A-5. Similar to the embodiment described previously, the reservoir component 404 is disposed laterally adjacent to the encasement 409 that includes the electronics component 406 and the battery component 408. The coil component 410 is disposed beneath the reservoir component 404 and is electrically coupled to the battery component 408 and/or the electronics component 406 via conductive leads extending into the encasement 409. In the illustrated example, however, the reservoir component 404 assumes a different shape than the example of FIGS. 4A-5. As shown in FIG. 6, the reservoir component 404 includes a body 405 defining a generally cylindrical shape. A generally circular septum 414 is disposed within the upper surface 405b of the body 405 of the reservoir component 404. In this embodiment, a clinician may access the reservoir component 404 by inserting a needle generally orthogonally to a patient's skin to pierce the septum 414 of the reservoir component 404 when the device 400 is implanted within a patient.

Figure 7:
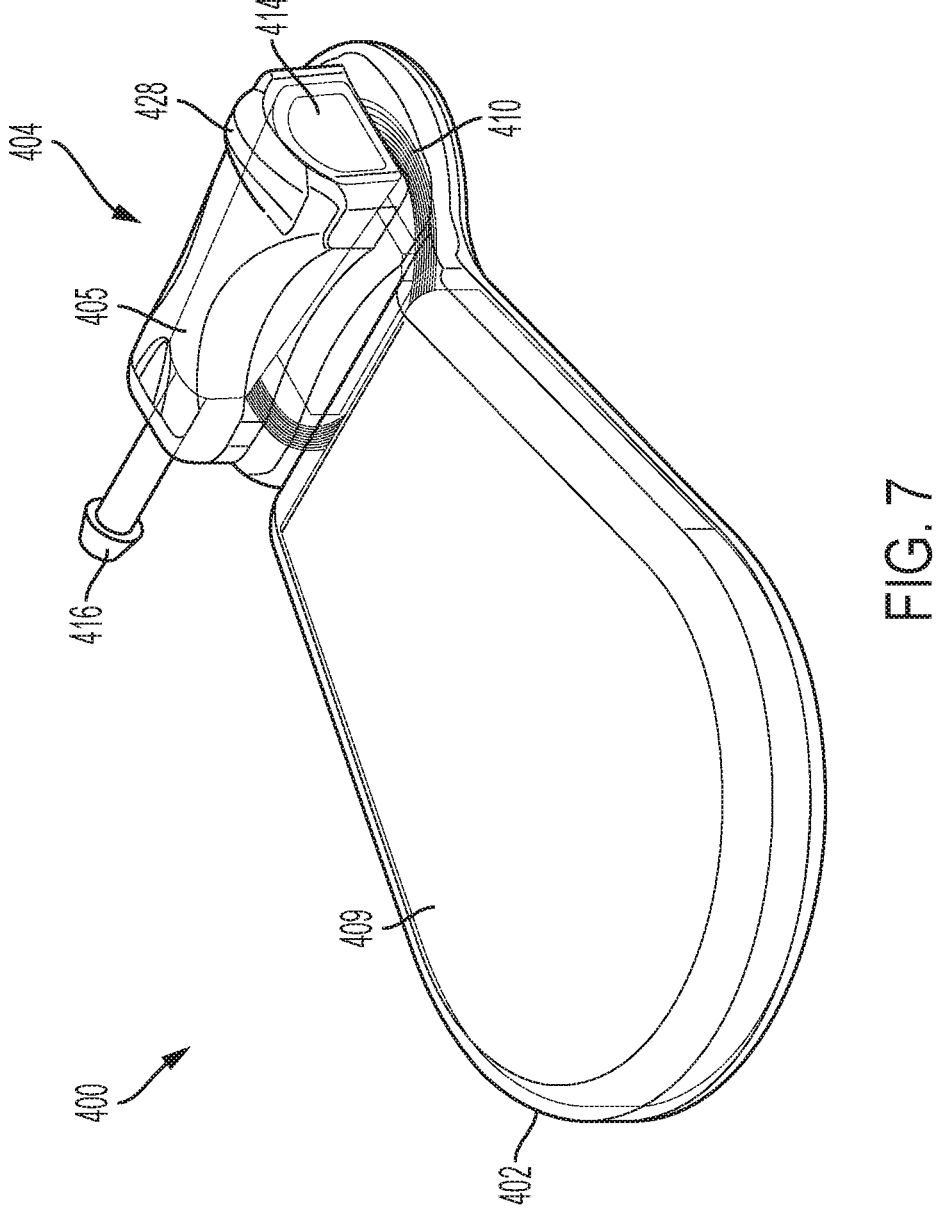
FIG. 7 illustrates another example vascular access device in accordance with the present technology.
Figure 8A:
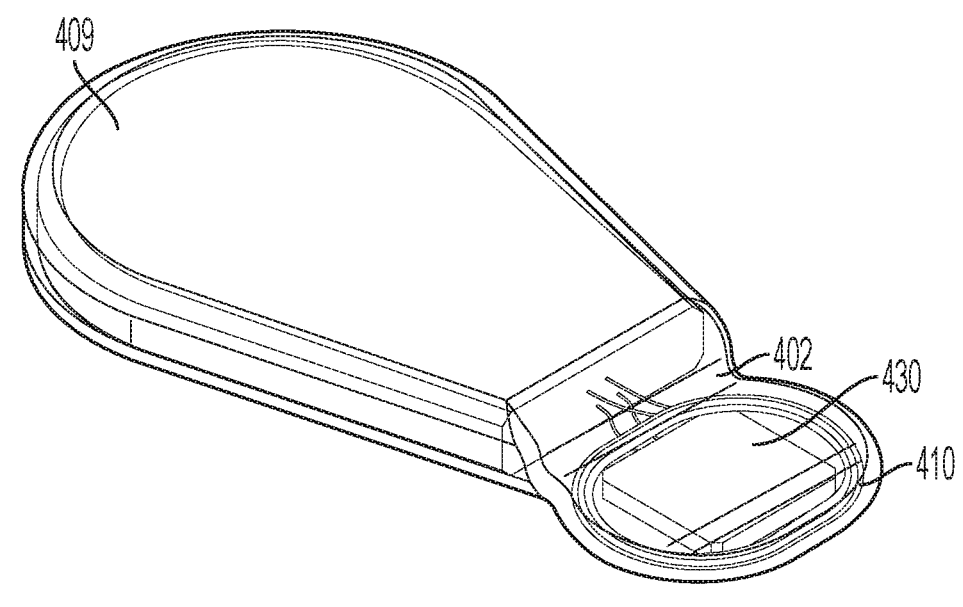
FIGS. 8A-8C illustrate top perspective, top, and bottom views, respectively, of the battery, electronic, and coil components of the vascular access device of FIG. 7.
Figures 8B, 8C:
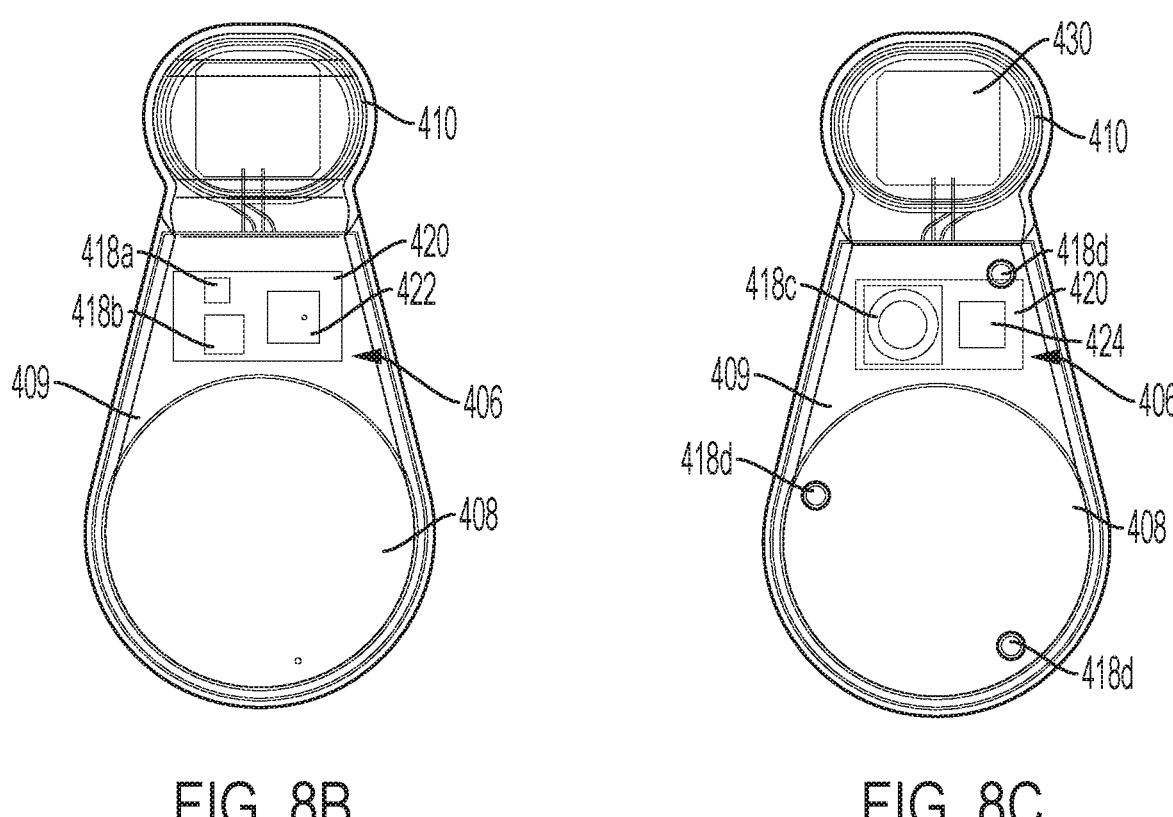
Figure 9A:
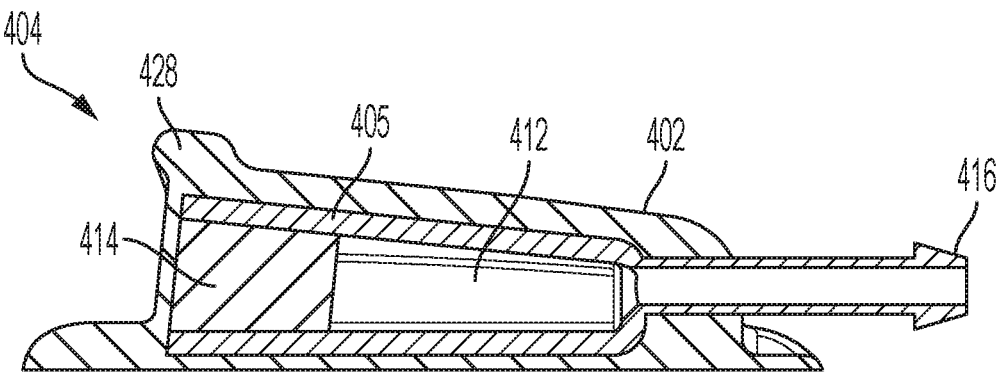
FIG. 9 illustrates side cross-sectional and top perspective views, respectively, of the reservoir component of the vascular access device of FIG. 7.
Figure 9B:
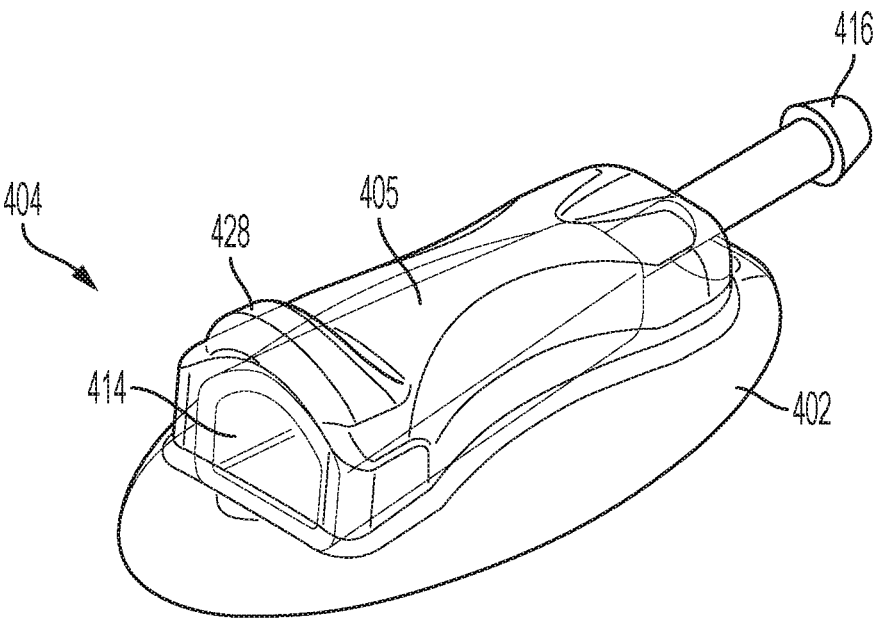

FIG. 7 illustrates another example vascular access device 400. FIGS. 8A-8C illustrate to top perspective, top, and bottom views, respectively, of the battery, electronic, and coil components of the vascular access device 400 of FIG. 7, and FIG. 9 illustrates side cross-sectional and top perspective views, respectively, of the reservoir component of the vascular access device 400 of FIG. 7. Referring to FIGS. 7-9 together, the encasement 409 that encloses the battery component 408 and the electronics component 406 has an irregular shape defining a generally flat aspect, with a wider rounded portion at a first end and a narrowed portion at a second that disposed adjacent to the reservoir component 404. As shown, the reservoir component 404 includes a septum 414 at a first end and an outlet port 416 at a second end having a barbed connector.

As seen in FIGS. 8A-8C, the device 400 can include a battery component 408 in the form of a substantially cylindrical battery. The electronics component 406 includes a printed circuit board 420 on which are mounted the wireless communication module 422, the wireless charging module 424, and a plurality of sensing elements 418a-d (which can include an accelerometer 418a, a temperature sensor 418b, a pulse oximeter 418c, and a plurality of EKG electrodes 418d). The device 400 can include a window disposed in the lower portion of the encasement 409 and/or the housing 402 and substantially aligned with the pulse oximeter 418c, such that optical signals can be transmitted between the pulse oximeter 418c and adjacent tissue or fluids when the device 400 is implanted within the body. Additionally, an antenna 430 (e.g., a Bluetooth Low Energy antenna) can be positioned beneath and/or within the coil component 410. This antenna can be part of the electronics component 406 and, in some embodiments, be electrically coupled to the wireless communication module 422.

The position and orientation of the septum 414 is such that, when the device is implanted within a patient, the axis of insertion of a needle into the septum 414 is acutely angled with respect to a patient's skin, and may resemble an angle of insertion for a standard IV needle as is familiar to clinicians. On the upper surface of the reservoir component 404 is a ridge 428 positioned over and substantially aligned with the septum 414. In some embodiments, this ridge 428 may provide an irregular surface that can be detected via palpation. Additionally, the body 405 of the reservoir component 404 can include narrower central portion or "saddle" grip to allow the device 400 to be held by a clinician through the skin during injection of the needle into the septum 414.

Figure 10:
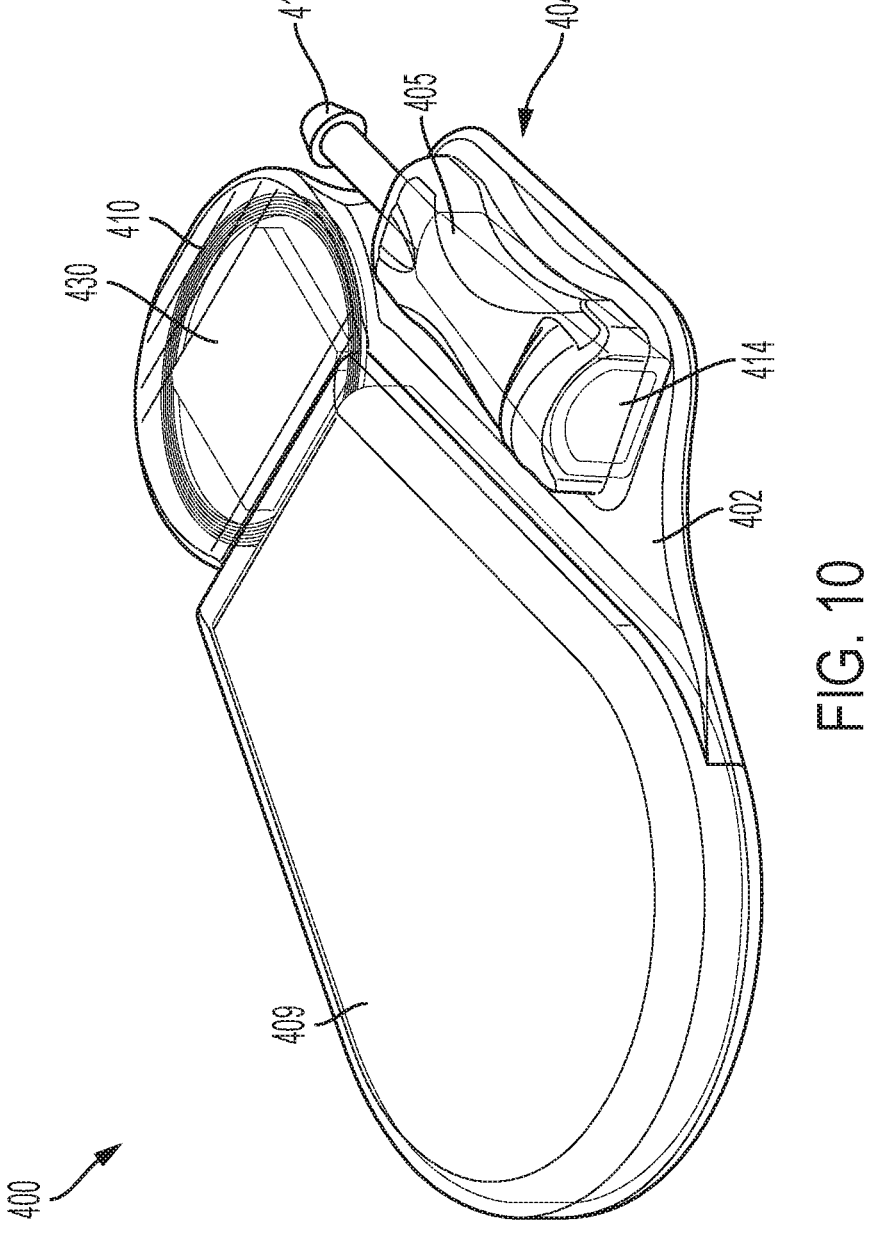
FIG. 10 illustrates another example vascular access device in accordance with the present technology.

FIG. 10 illustrates another example vascular access device 400. The embodiment illustrated in FIG. 10 can be substantially similar to that described above with respect to FIGS. 7-9, except that the reservoir component 404 can be positioned laterally adjacent a long edge of the encasement 409, rather than at a distal position axially aligned with the encasement 409 as in the previously described embodiment. As compared to the embodiment of FIGS. 7-9, the embodiment shown in FIG. 10 may have a larger footprint but a lower profile since the reservoir component 404 is not stacked vertically over the coil component 410. In some cases, this may improve patient comfort by reducing protrusion of the device 400 through the patient's skin. In some embodiments, the outer housing 402 may be sufficiently flexible such that the reservoir component 404 can flex or deform relative to the encasement 409 and/or the portion of the housing 402 enclosing the coil component 410. Such flexing can further improve patient comfort.

Figure 11A:
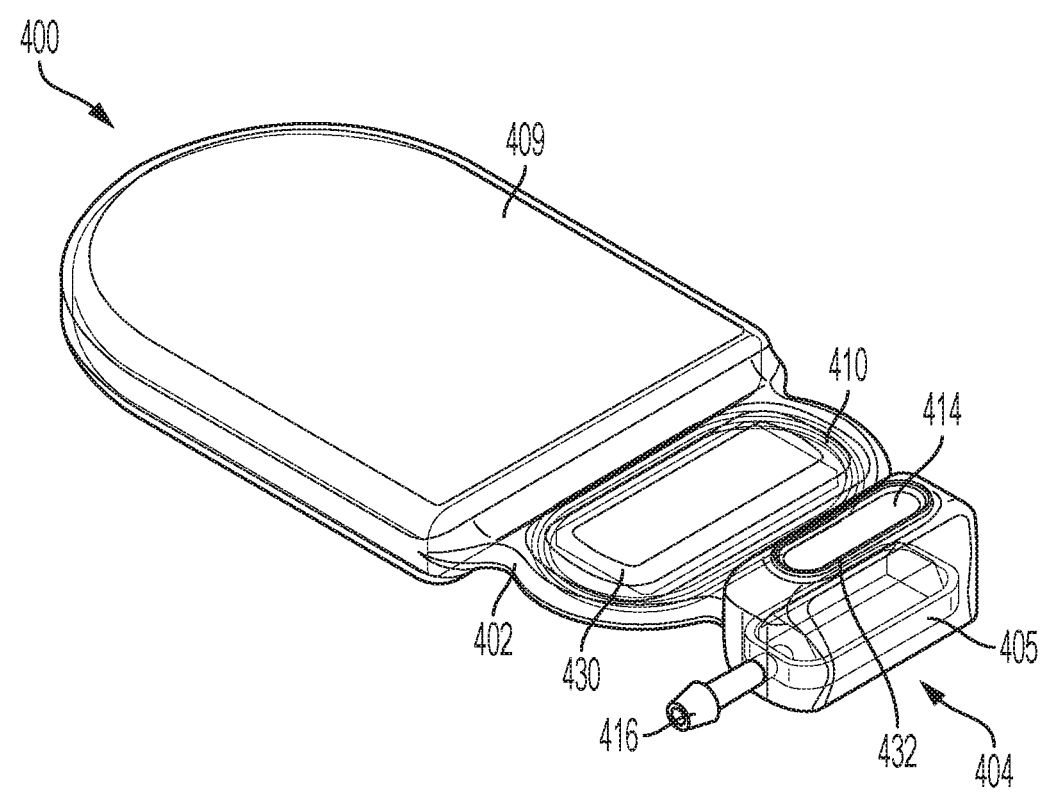
FIGS. 11A and 11B illustrate top perspective and bottom views, respectively, of another example vascular access device in accordance with the present technology.
Figure 11B:
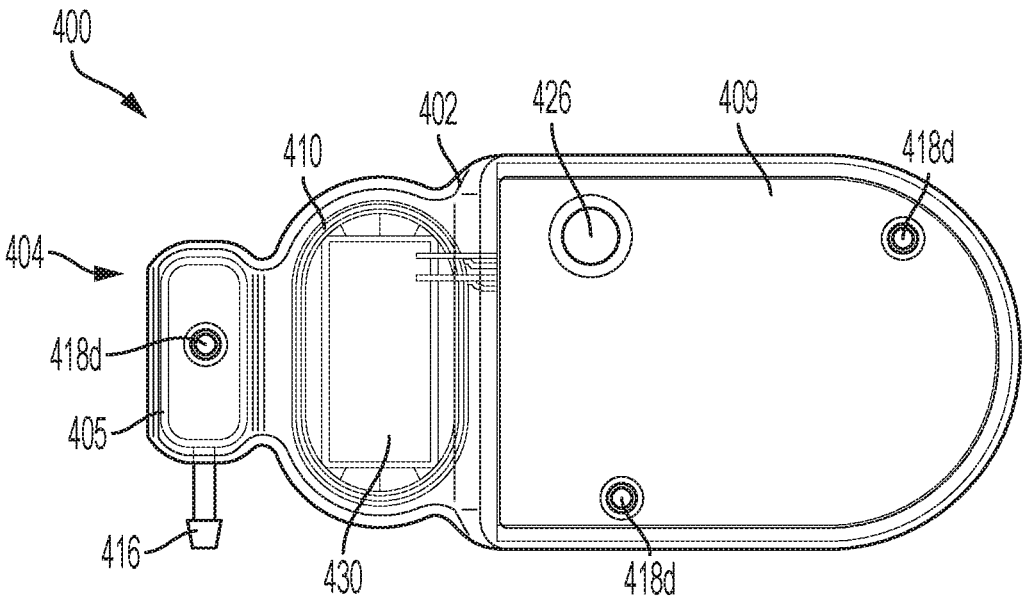

FIGS. 11A and 11B illustrate top perspective and bottom views, respectively, of another example vascular access device 400. The embodiment illustrated in FIGS. 11A and 11B can be similar to that of FIGS. 7-11 except that the reservoir component 404 is positioned at one end of the device 400 such that the coil component 410 and the antenna 430 are positioned between the encasement 409 and the reservoir component 404. Additionally, the reservoir component 404 has a body 405 defining a generally rectangular shape, with a raised rim 432 disposed over the upper surface. This raised rim 432 can be palpable and surround the septum

414, allowing a clinician to more easily locate and access the reservoir component 404 of the device 400.

Figure 12A:
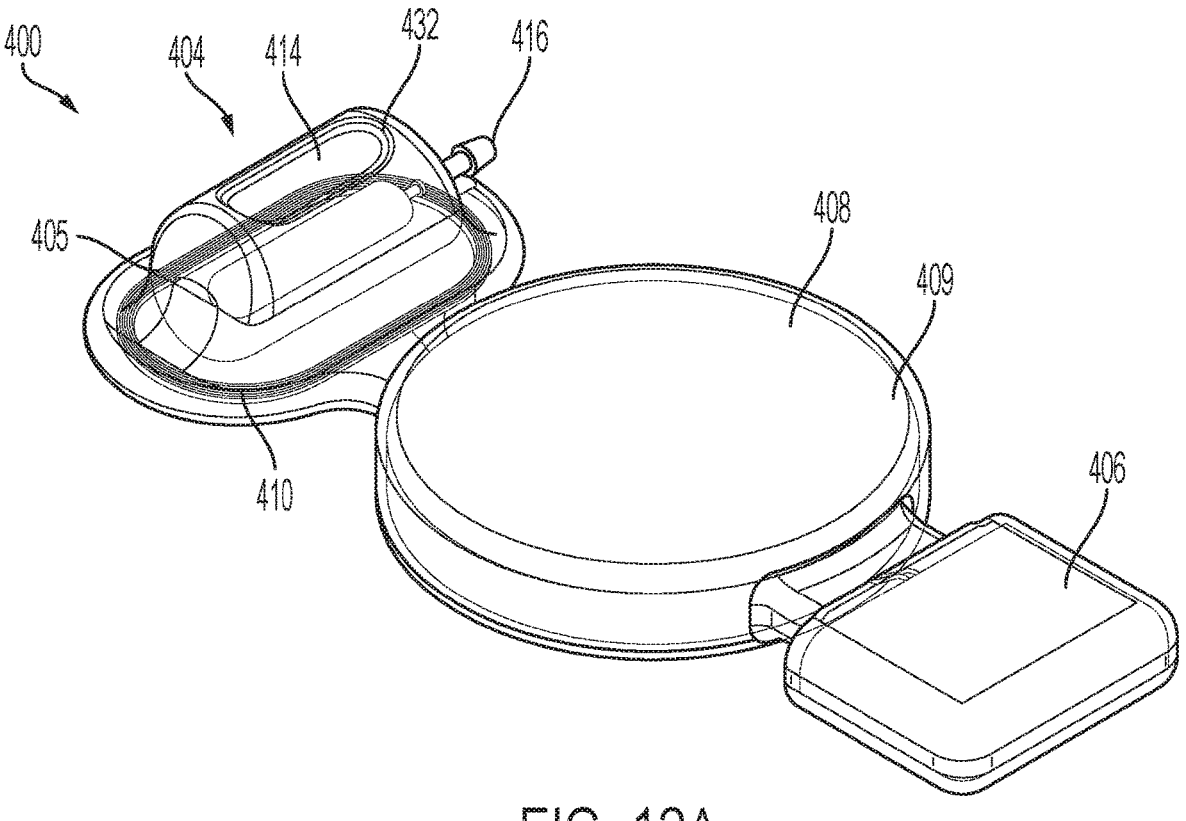
FIGS. 12A-12C illustrate top perspective, top, and bottom views, respectively, of another example vascular access device in accordance with the present technology.
Figure 12B:
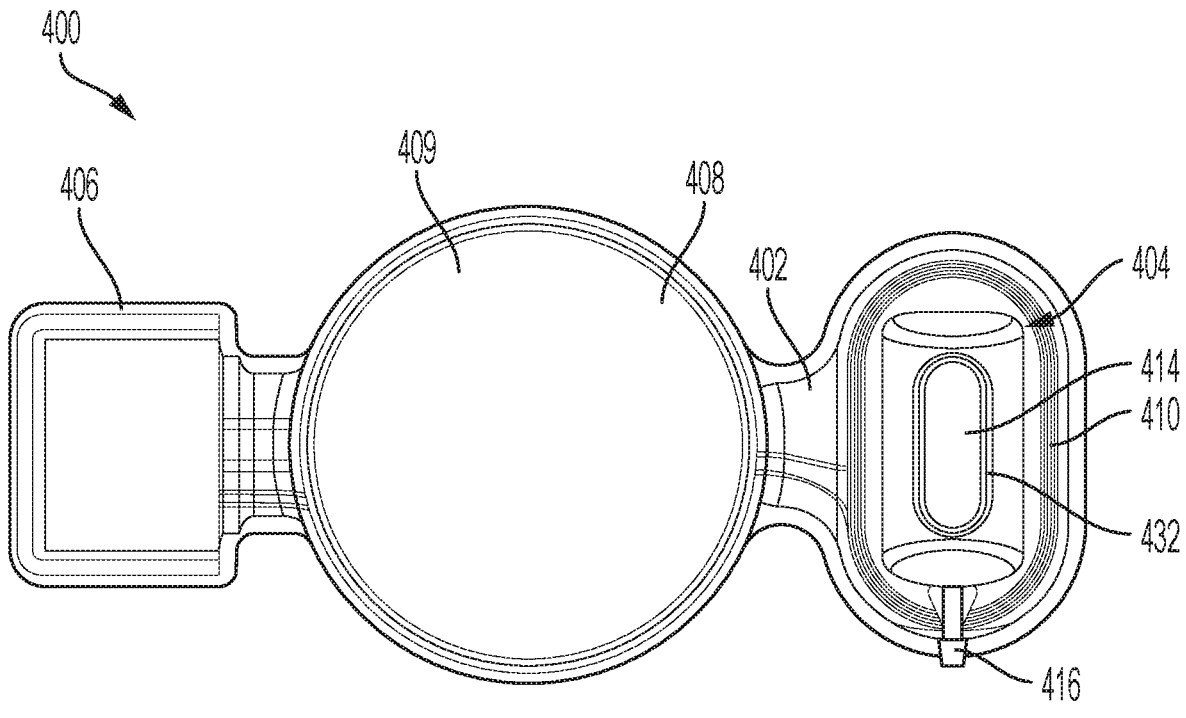
Figure 12C:
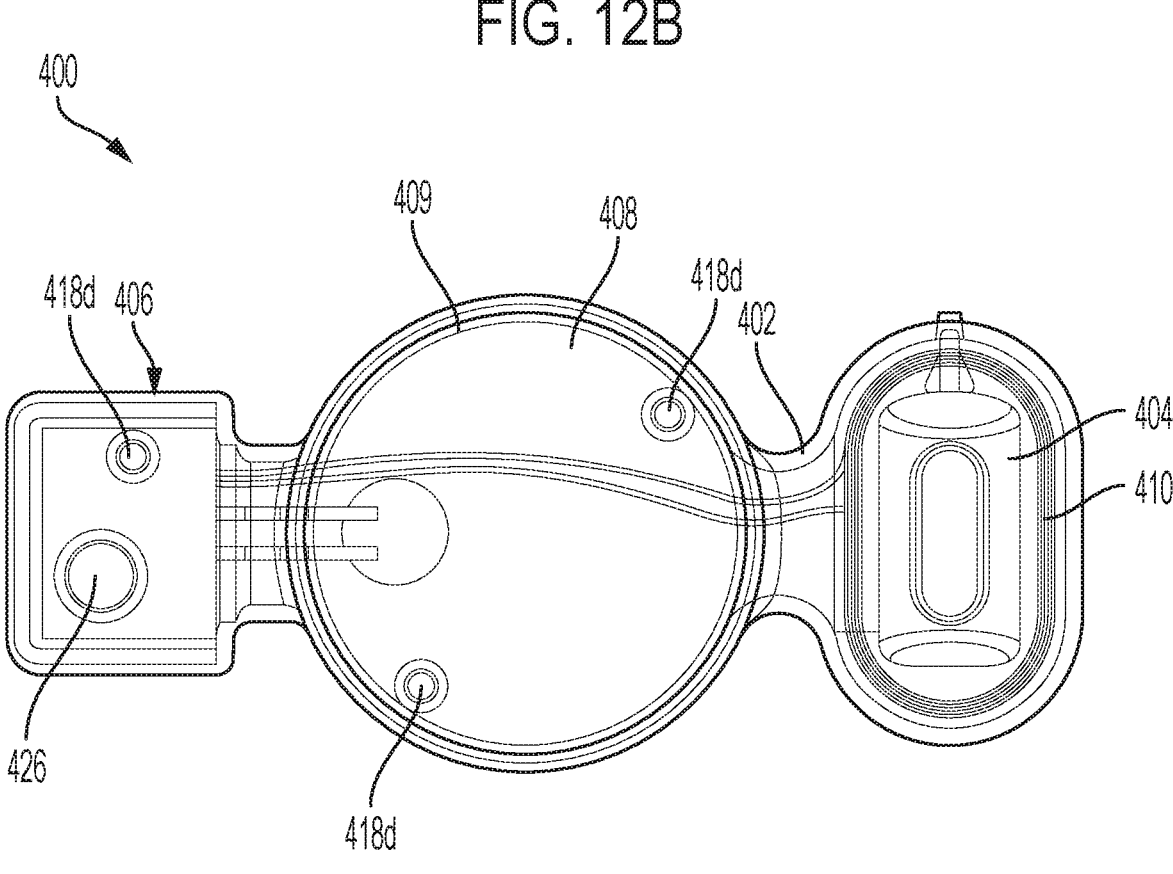

FIGS. 12A-12C illustrate top perspective, top, and bottom views, respectively, of another example vascular access device 400. The illustrated device 400 can be similar to that described above with respect to FIGS. 11A-B except that, in this embodiment, the electronics component 406 is laterally separated from the battery 408 and the two are not enclosed within the single encasement 409. Rather, the battery component 409 is disposed within the encasement 409, and the electronics component 406 is positioned separately and laterally displaced from the battery component 408. The reservoir component 404 is positioned on an opposite side of the device. The housing 402 encompasses the entire device 400 and mechanically connects the reservoir component 404 (which overlies the coil component 410), the battery component 409, and the electronics component 406. The housing 402 can be flexible such that the three segments are able to at least partially flex or bend with respect to one another. This movement may increase patient comfort by providing less resistance to patient movement or unwanted protrusion of the device.

FIGS. 13A-17D illustrate additional examples of a vascular access device 400 in which the coil component 410 has been omitted. In these examples, the device 400 includes a reservoir component 404, a battery component 406, and an electronics component 408 similar to those described above with respect to FIGS. 4A-12C.

Figure 13A:
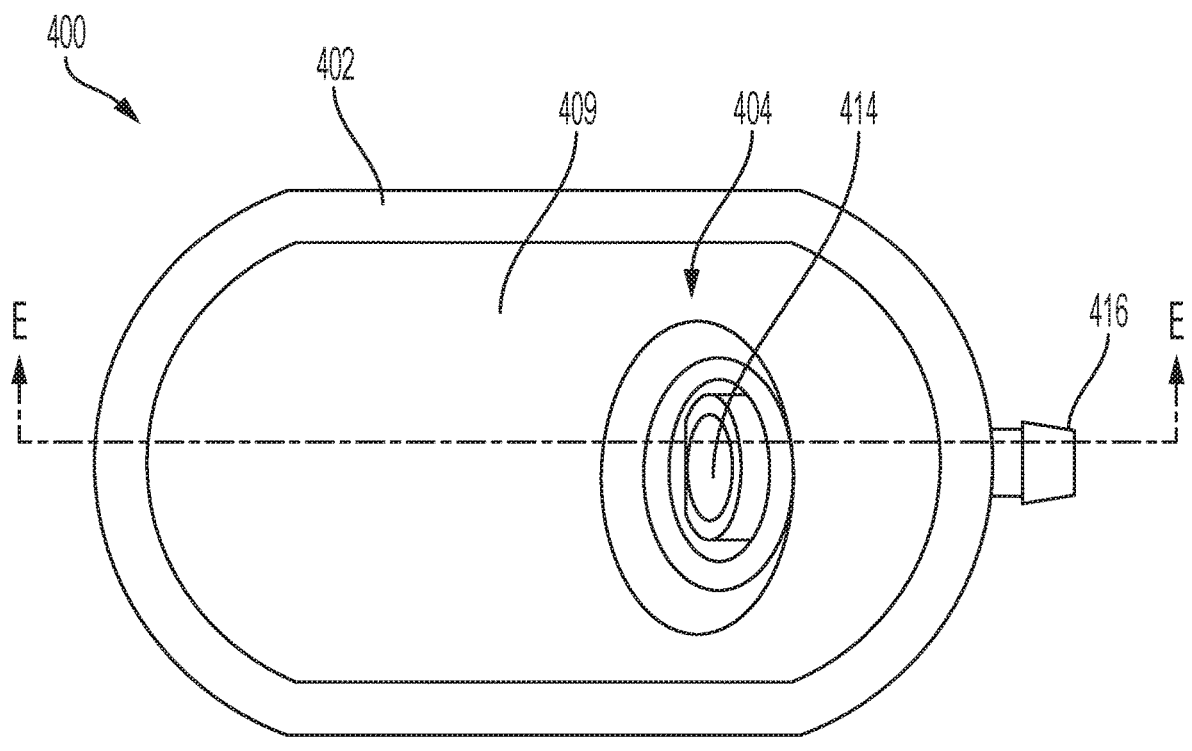
FIGS. 13A and 13B illustrate top and side cross-sectional views, respectively, of another example vascular access device in accordance with the present technology.
Figure 13B:
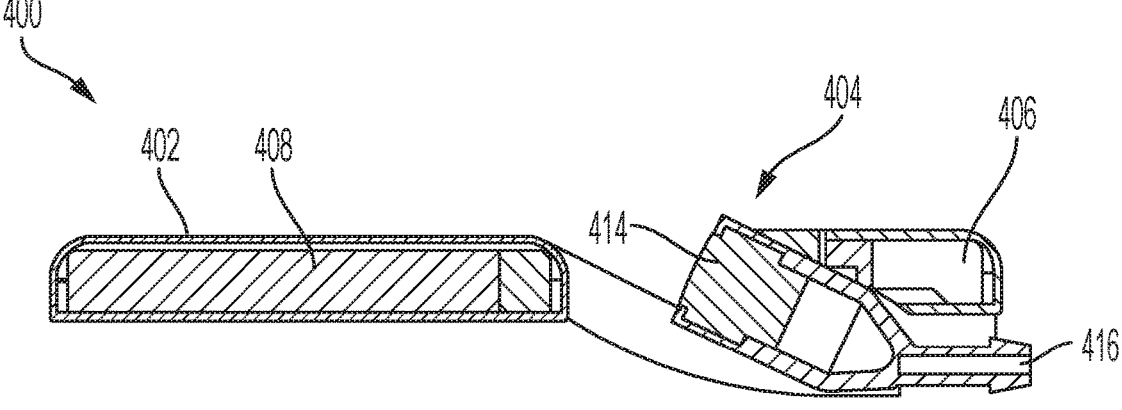
Figures 14A, 14B, 14C, 14D:
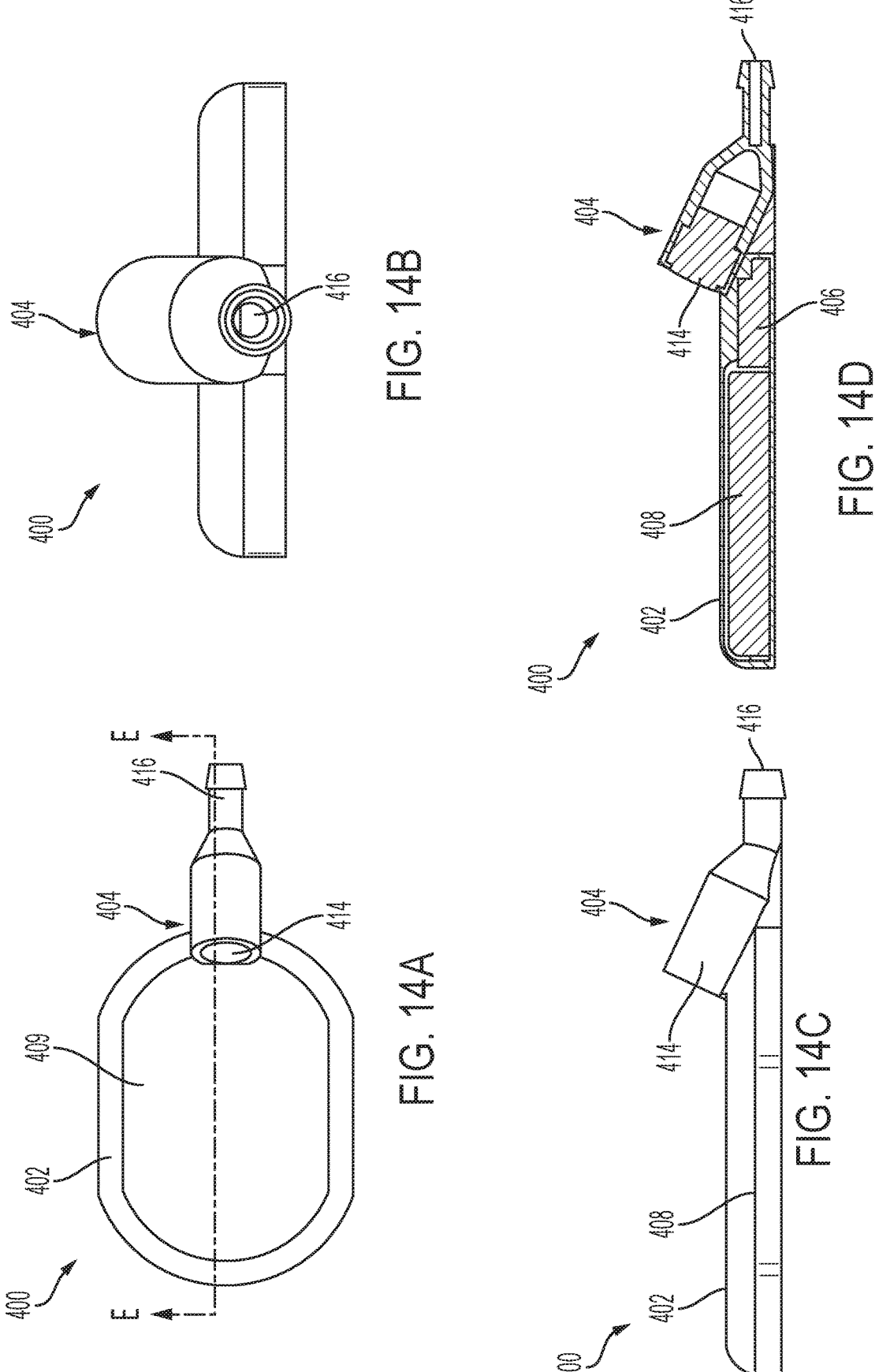
FIGS. 14A-14D illustrate top, front, side, and side cross-sectional views, respectively, of another example vascular access device in accordance with the present technology.

Referring to FIGS. 13A and 13B, the device 400 has a staggered shape such that the reservoir component 404 is recessed relative to the battery component 408. The reservoir component 404 can also include an angled funnel in which the septum 414 is disposed allowing for angled insertion of a needle through the septum 414. This recessed configuration can reduce protrusion of any portion of the device 400, thereby reducing patient discomfort and eliminating or reducing any visible indication of the device on a patient's skin.

FIGS. 14A-14D illustrate top, front, side, and side cross-sectional views, respectively, of another example vascular access device 400. The illustrated embodiment can be similar to that shown in FIGS. 13A and 13B, except here the reservoir portion 404 is not recessed relative to the battery portion 408. Rather, the bottom of the entire device 400 is planar and the septum 414 of the reservoir portion 404 protrudes above the surface of the battery component 408.

Figure 15A:
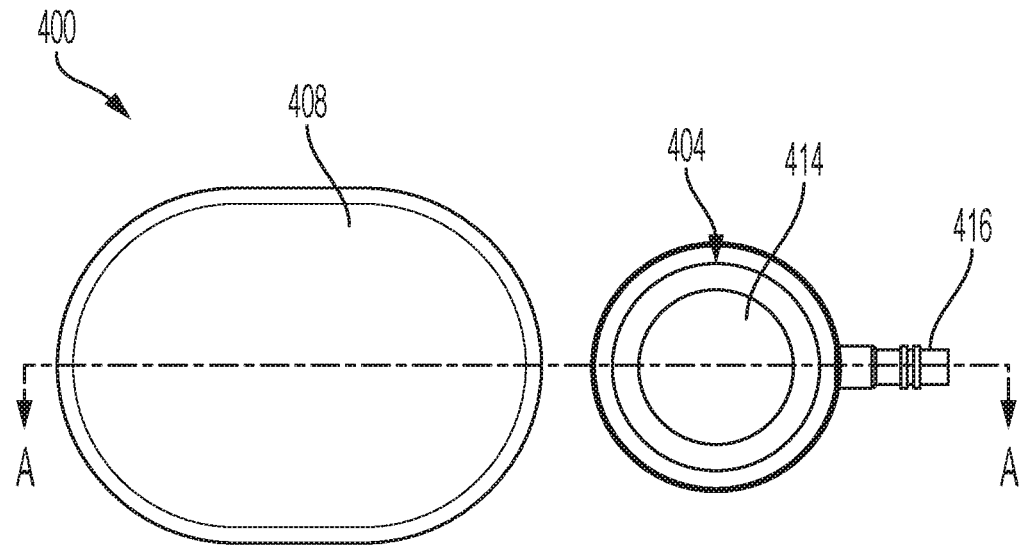
FIGS. 15A and 15B illustrate top and side cross-sectional views, respectively, of another example vascular access device in accordance with the present technology.
Figure 15B:
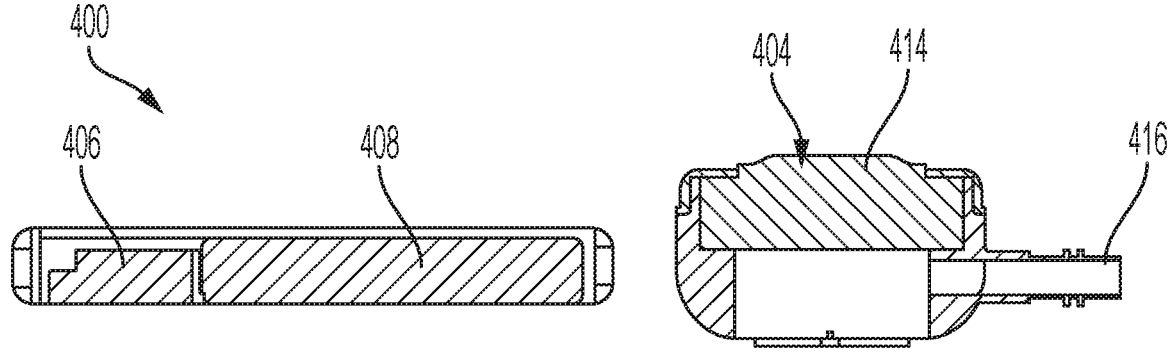

FIGS. 15A and 15B illustrate top and side cross-sectional views, respectively, of another example vascular access device 400. In this example, the battery component 408 and the electronics component 406 can be housed together in a portion that is physically separated from the reservoir component 404. In some embodiments, the two components can be connected via a flexible tether or substrate to allow relative movement between the two. As illustrated, the reservoir component 404 can include a generally cylindrical body with the septum 414 disposed over the upper surface, and the outlet port 416 extending laterally away from a side of the reservoir component 404.

Figure 16A:
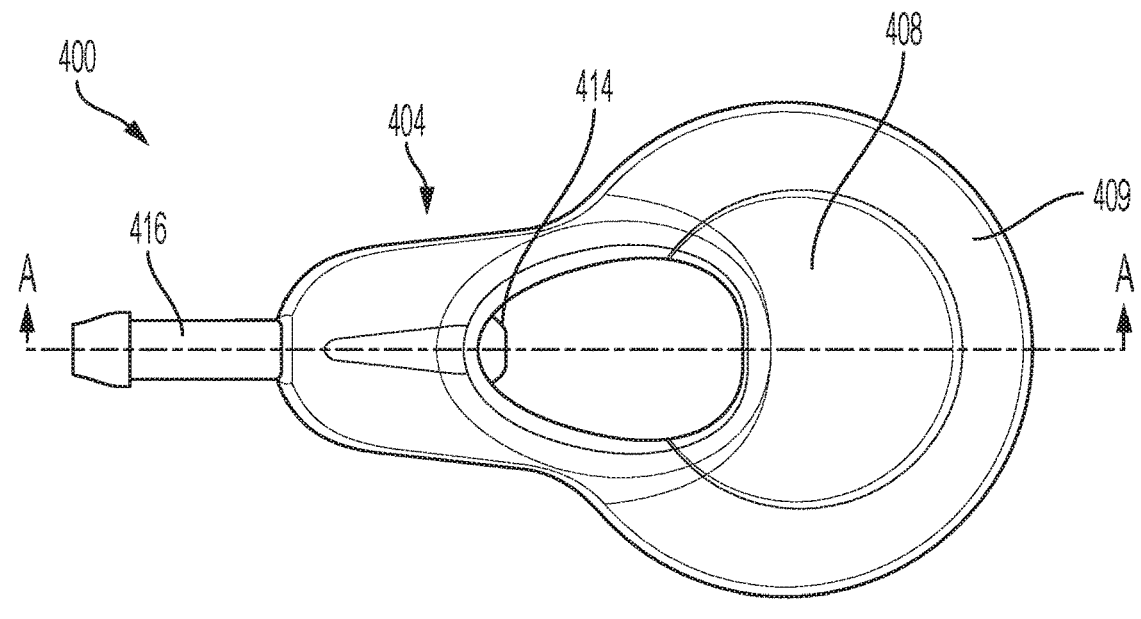
FIGS. 16A-16C illustrate top, side, and side cross-sectional views, respectively, of another example vascular access device in accordance with the present technology.
Figure 16B:
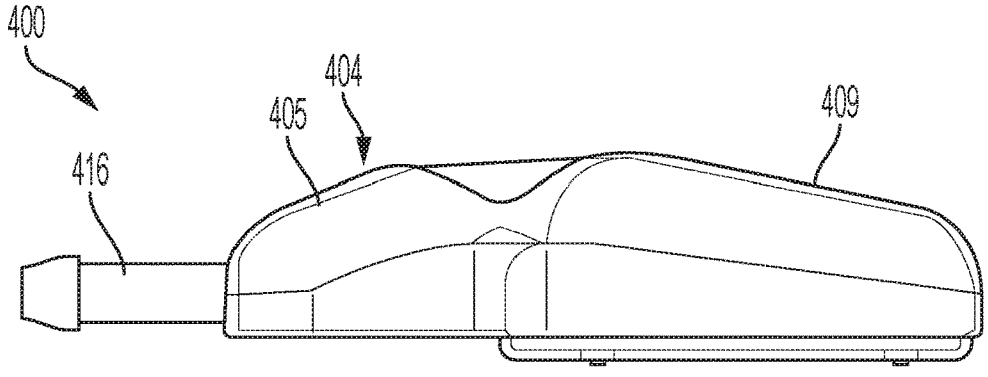
Figure 16C:
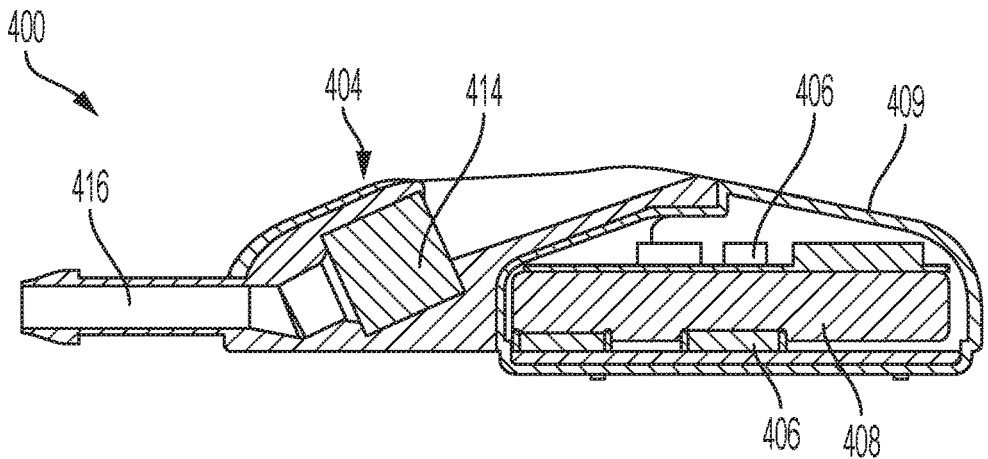
Figures 17A, 17B, 17C, 17D:
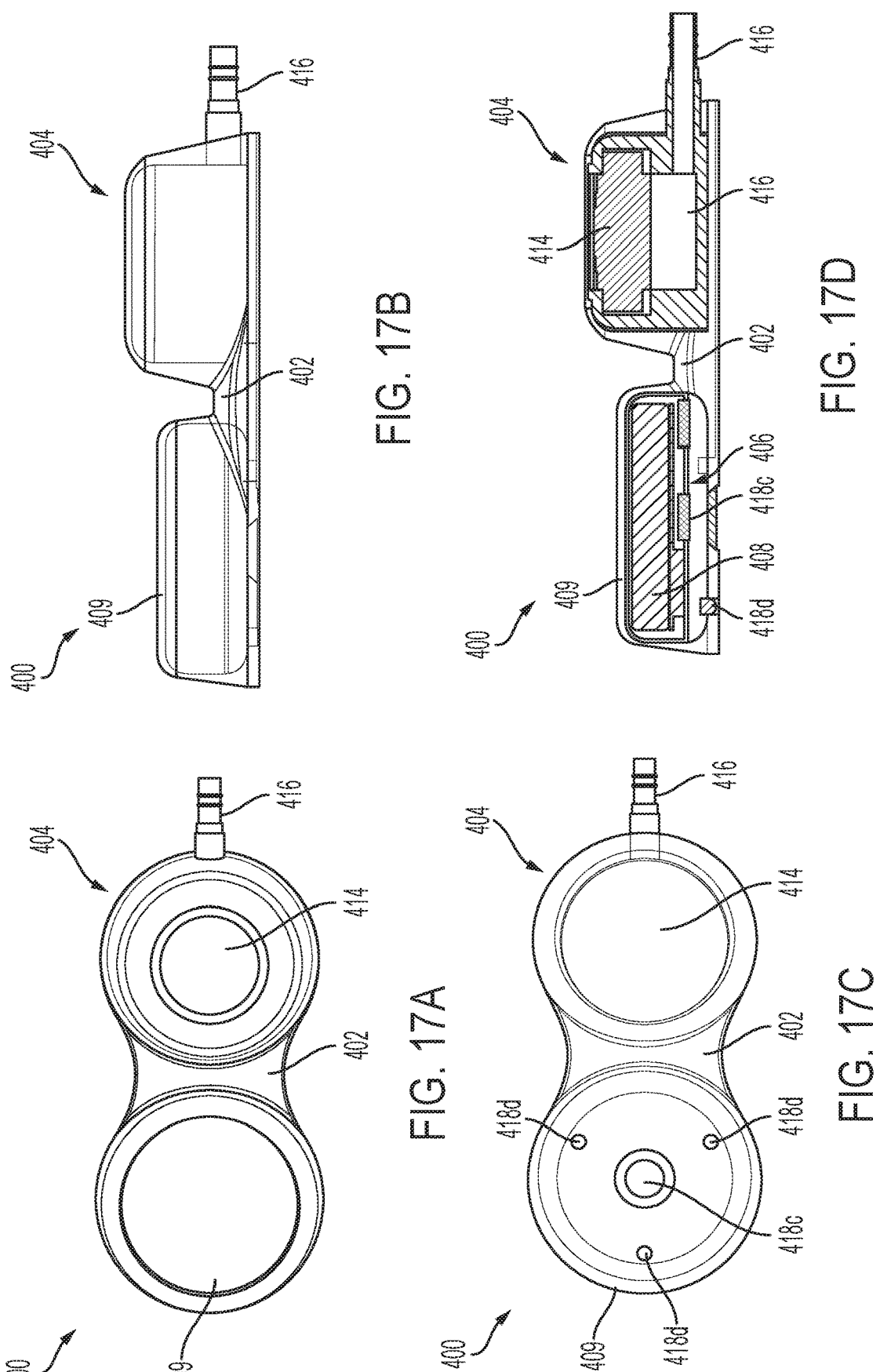
FIGS. 17A-17D illustrate top, side, bottom, and side cross-sectional views, respectively, of another vascular access device in accordance with the present technology.

FIGS. 16A-16C illustrate top, side, and side cross-sectional views, respectively, of another example vascular access device 400. The illustrated embodiment has an oblique layout with the battery component 408 and the electronics component 406 disposed at a first, wider end and the outlet port 416 of the reservoir component 404 disposed at a second, narrower end. The reservoir component 404 can also include an angled funnel in which the septum 414 is disposed allowing for angled insertion of a needle through the septum 414.

FIGS. 17A-17D illustrate top, side, bottom, and side cross-sectional views, respectively, of another vascular access device 400. This example includes two connected portions forming a "FIG. 8" shape in which the first portion includes the encasement 409 housing the battery component 408 and the electronics component 406 (which includes the sensing elements 418). The second portion, connected to the first via a segment of the housing 402, includes the reservoir component 404, which here has a generally cylindrical shape with the septum 414 disposed at the upper end of the reservoir portion 404. In some embodiments, the segment of the housing 402 connecting the two portions can be flexible to allow relative movement between the two.

Figure 18A:
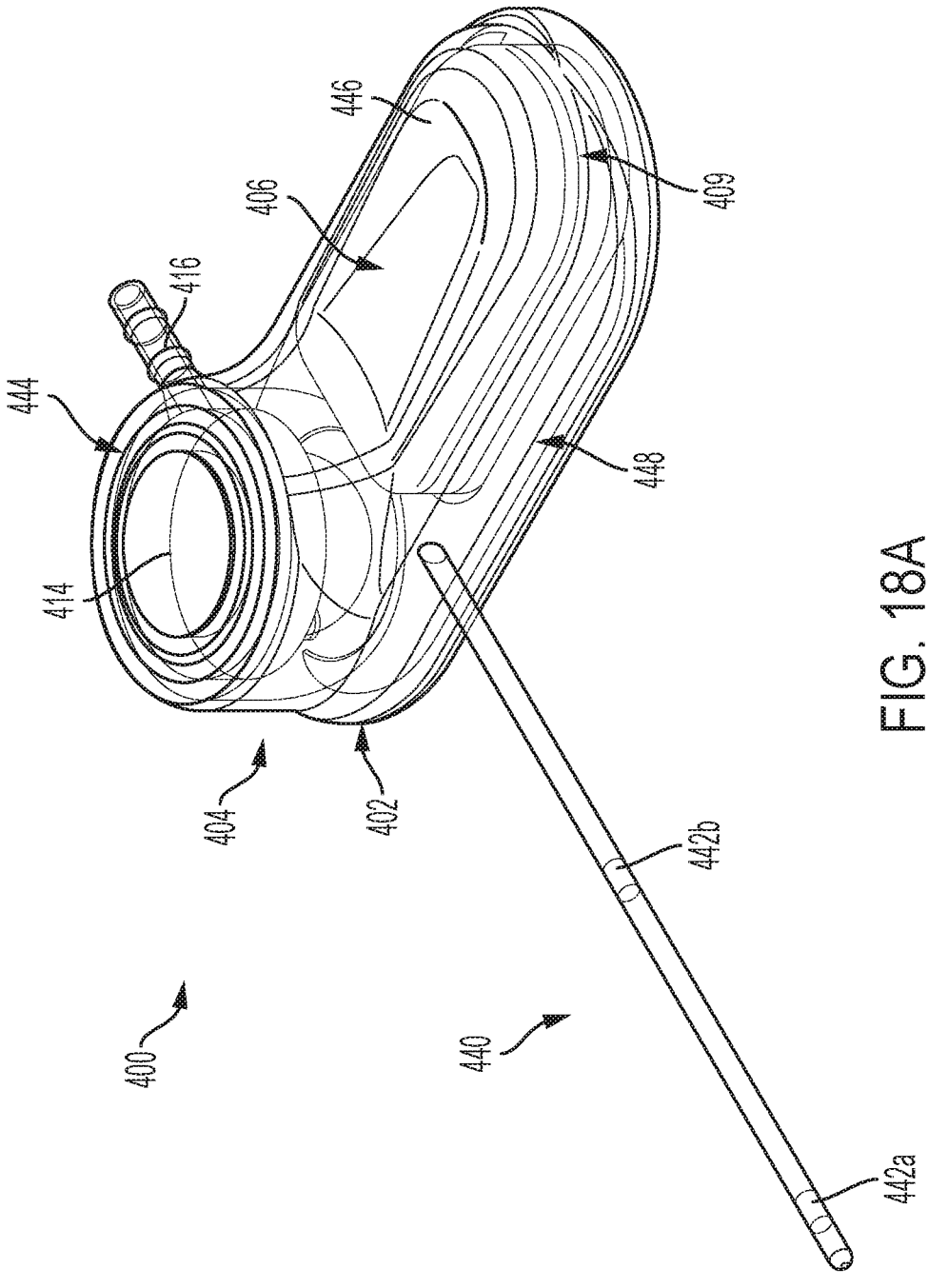
FIGS. 18A and 18B illustrate isometric and side views, respectively, of another vascular access device in accordance with the present technology.
Figure 18B:
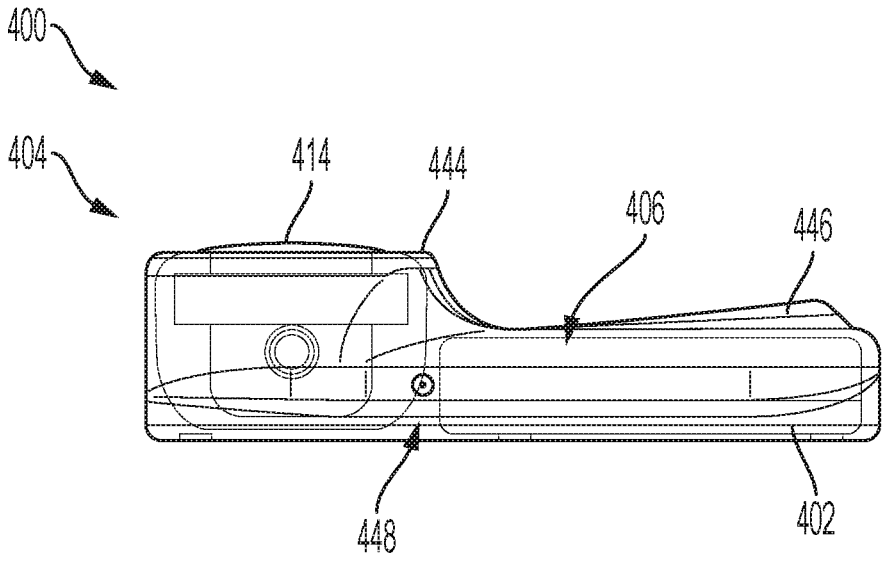
Figure 19A:
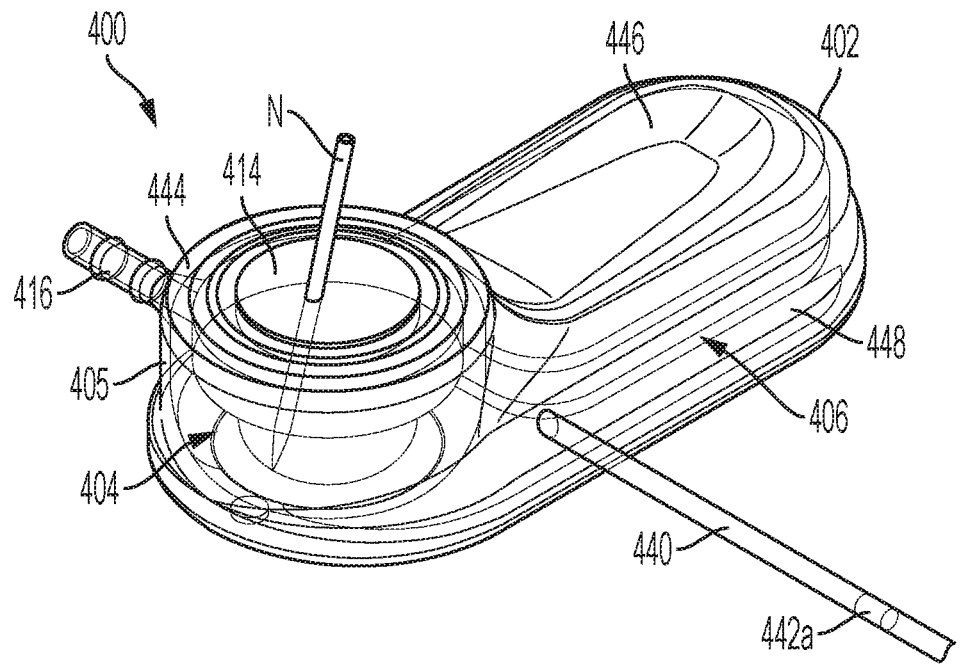
FIGS. 19A and 19B illustrate isometric and cross-sectional side views, respectively, of the vascular access device shown in FIGS. 18A and 18B, shown with a needle delivered through the septum into the reservoir of the device.
Figure 19B:
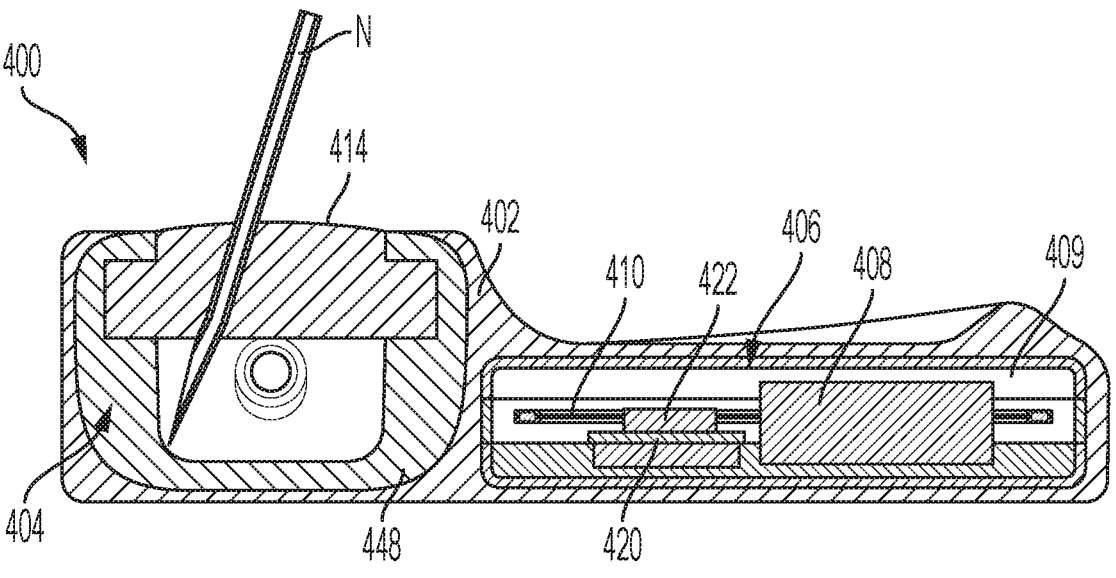

FIGS. 18A and 18B illustrate isometric and side views, respectively, of another vascular access device 400 in accordance with the present technology. FIGS. 19A and 19B illustrate isometric and cross-sectional side views, respectively, of the vascular access device 400 with a needle N delivered through the septum 414 into the interior of the reservoir 404. Similar to the embodiment described in FIG. 6, the reservoir component 404 is disposed laterally adjacent the electronics component 406. The device 400 further includes a lead 440 extending away from the housing 402 and having first and second electrodes 442*a* and 442*b* (collectively referred to as "the electrodes 442"). When implanted in the body, at least a portion of the lead 440 and the electrodes 442 are in direct contact with bodily tissue or fluids. The electrodes 442 may be electrically coupled to the electronics component 406 via the lead 440. For example, the electrodes 442 may be electrically coupled to a processing unit or other suitable module for receiving, processing, and storing measurements from the electrodes 442 to determine one or more physiological parameters, such as heart rate, respiratory rate, etc.

In some embodiments, it may be beneficial for the lead 440 to protrude from a side of the device 400 opposite that of the outlet port 416 to avoid entanglement with any tubing coupled to the outlet port 416. Additionally, the positioning of the lead 440 opposite the outlet port 416 enables the device 400 to be implanted in an orientation such that the lead 440 extends inferiorly and generally aligned with the axis of depolarization of the heart, and thus maximizing electrical signal detection. The lead 440, for example, may extend from a portion of the housing 402 between reservoir 404 and the electronics component 406 (or otherwise aligned with the adjacent portions of the reservoir 404 and electronics component 406). In other embodiments, the lead 440 may extend from any portion of the sides, top, or bottom of the housing 402.

As shown in FIG. 18A, in some embodiments the lead 440 may extend generally orthogonal to the length of the housing 402 within generally the same plane as the housing 402 (as shown) at least before the device 400 is implanted. In other embodiments the lead 440 may extend at a non-orthogonal angle relative to the length housing 402. In any of the foregoing embodiments, the lead 440 may extend upwards or downwards relative to the housing 402. Although the device 400 includes two electrodes 442, in other embodiments the device 400 may include a single electrode or more than two electrodes. Likewise, although the device 400 includes a single lead 440, in other embodiments the device 400 may include multiple leads, each of which may include a single electrode or multiple electrodes. According to some embodiments, the lead 440 is made of a flexible material so as to enable conformity to underlying anatomy when placed within the body.

In some embodiments, the lead 440 is arranged so that, when the device 400 is implanted within the body, the lead 440 extends inferiorly with respect to the housing 402. Additionally, the lead 440 can be arranged so as to provide a spacing between the first electrode 442*a* and the second electrode 442. In operation, a greater distance between the electrodes may improve the signal to noise ratio for cardiac rhythm monitoring. Additionally, because the pocket incision for implanting the device 400 is created from the superior aspect and dissected inferiorly, a tunneling device could be used to dissect a pathway for the lead 440 in the subcutaneous tissues. Moreover, placing the electrodes 442 in this configuration aligns the lead 440 somewhat with the depolarization vector of the interventricular septum of the heart, the main pathway of conduction, allowing for improved signal detection.

The device 400 may also include one or more topographical features that can be detected via palpation. The features are configured to aid a clinician in locating the device 400 under the patient's skin and/or determining the relative orientation of the device 400 and/or one or more components of the device 400. For example, the device 400 may include a ramped portion 446 superimposed with a portion of the electronics component 406. As best shown in FIGS. 18A and 18B, a height of the ramped portion 446 may increase in a direction away from the reservoir 404, and may also increase towards the lateral edges of the device 400. In some embodiments, the ramped portion 446 is generally u-shaped with the curved portion concave towards the reservoir 404. Such a feature may be beneficial for helping a clinician locate the device 400 and/or determine a midline of the device 400. Additionally or alternatively, the device 400 may include an annular ridge 444 surrounding all or a portion of the circumference of the septum 414. Locating the ridge 444 via palpation or other means can help guide a clinician when inserting a needle through the septum 414.

Additionally or alternatively to the ramped portion 446 and/or ridge 444, localization features can assume other forms, for example bumps, beads, protrusions, depressions, or any other suitable topographical features that facilitate localization via palpation. In some embodiments, such topographical features can be substantially omitted, and localization can be facilitated using other approaches, for example lights, electromagnetic sensors, etc.

In some embodiments, the topographical features may be formed of the housing 402. For example, for any of the vascular access device embodiments describe herein, the housing 402 may be formed of a soft sheath (such as a soft silicone overmold) that encapsulates at least the reservoir component 404 and the electronics component 406. The sheath may be molded to include the topographical features, or may moldable such that the sheath allows a feature or protrusion of an underlying, more rigid structure to protrude (with the sheath still covering). In the embodiment shown in FIGS. 18A-19B, the lead 440 extends through an opening in the housing 402. The use of a soft, malleable mold provides structure to the device 400 while also providing comfort for the patient and some degree of flexibility so that the device 400 fits better within a patient's anatomy.

In some embodiments, the device 400 may include a suture reinforcement 448 extending along all or a portion of the housing 402. This suture reinforcement may be a fine and flexible material, such as a mesh, that is embedded within the housing 402. An operator can place a suture, tack, screw, or other fixation means through any portion of the reinforcement 448 to provide stability and anchoring to underlying anatomic structures.

Referring to FIG. 19B, a coil component (e.g., coil component 410 described elsewhere herein) may be positioned within the encasement 409 and surround the other elements within the encasement 409. In other embodiments, a coil component (may be disposed beneath the reservoir component 404 and is electrically coupled to the battery component 408 and/or the electronics component 406 via conductive leads extending into the encasement 409. In the illustrated embodiment, the battery component 408 is disc-shaped and thus has a lower profile than the cylindrical embodiments described above. In still other embodiments, the coil component can be omitted entirely.

The electronics component 406 can include a plurality of individual elements mounted to one or both sides of the printed circuit board (PCB) 420. In any of the embodiments described herein, the device 400 may include multiple PCBs which may be distributed horizontally or vertically. The elements included with the electronics component 406 may include one or more of a wireless communication module 422 (e.g., a Bluetooth Low Energy chip or similar module configured to enable short-range or long-range wireless communication between the device 400 and one or more remote computing devices), any of the sensing elements described above with reference to FIGS. 4A-17D (such as a pulse oximeter, a temperature sensing element, etc.), and a wireless charging module (e.g., a wireless power receiver chip) (not shown). As described above, any of the sensing elements may be at least partially exposed through the encasement 409 and/or housing 402 such that, when the device 400 is implanted, the sensing elements are exposed to biological tissue or fluids and/or make any necessary measurements with the surrounding tissue and/or fluids. For example, the device 400 can include a window (not shown) disposed in the lower portion of the encasement 409 and/or the housing 402 and substantially aligned with one or more of the sensing elements, such as a pulse oximeter, such that optical signals can be transmitted between the respective sensing element and adjacent tissue or fluids when the device 400 is implanted within the body.

As shown in FIGS. 19A and 19B, a clinician may access the reservoir component 404 by inserting a needle N generally orthogonally (e.g., within about 15 degrees of orthogonal) to the septum 414 when the device 400 is implanted within a patient.

Figure 20A:
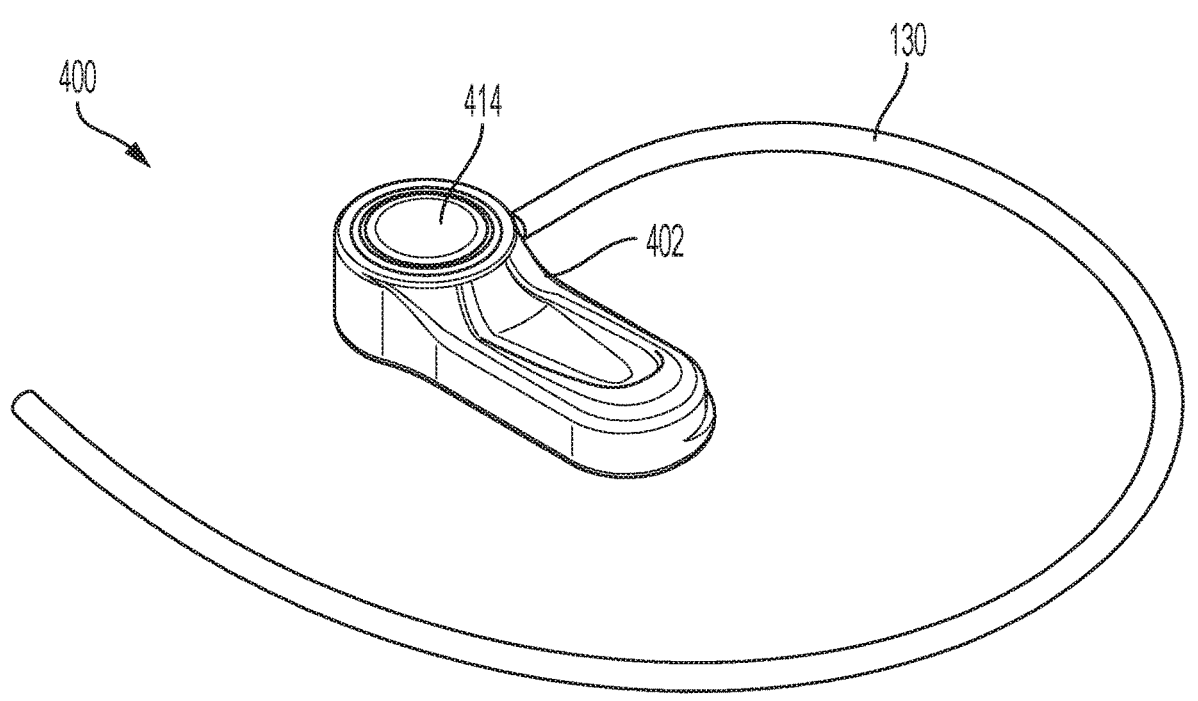
FIGS. 20A and 20B illustrate two isometric views of another vascular access device in accordance with the present technology.
Figure 20B:
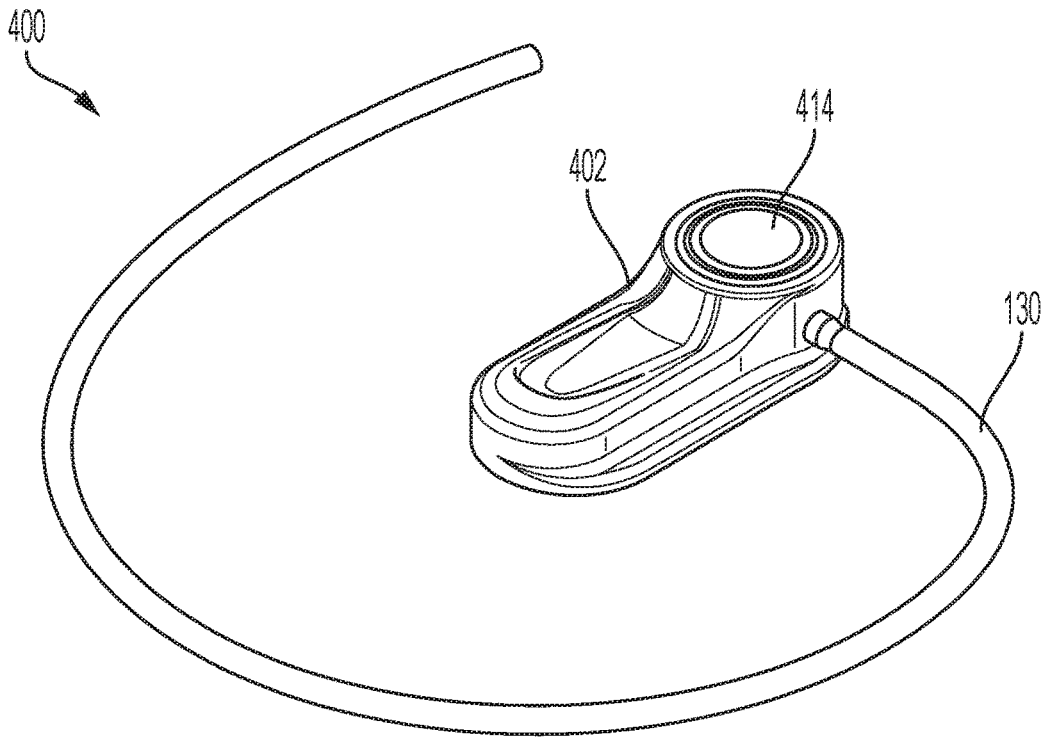

FIGS. 20A and 20B illustrate two isometric views of another vascular access device 400 in accordance with the present technology. The device 400 shown in FIGS. 20A and 20B can be substantially the same as the device described above with respect to FIGS. 18A-19B, except that the device 400 shown in FIGS. 20A and 20B excludes the lead 440. As shown in FIGS. 20A and 20B, a catheter 130 can be mated (e.g., removably coupled) to the device 400 by inserting one end of the catheter 130 over the outlet port 416.

Selected Examples of Implantable Patient Monitoring Devices

Figure 21A:
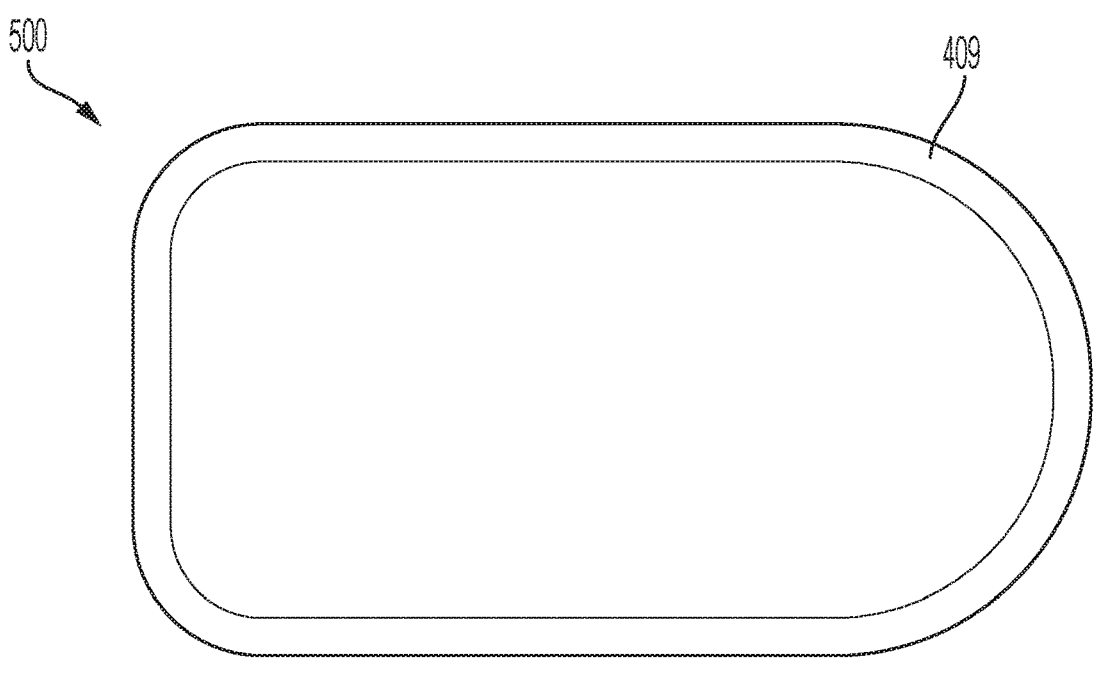
FIGS. 21A and 21B illustrate top and bottom views, respectively, of a monitoring device in accordance with the present technology.
Figure 21B:
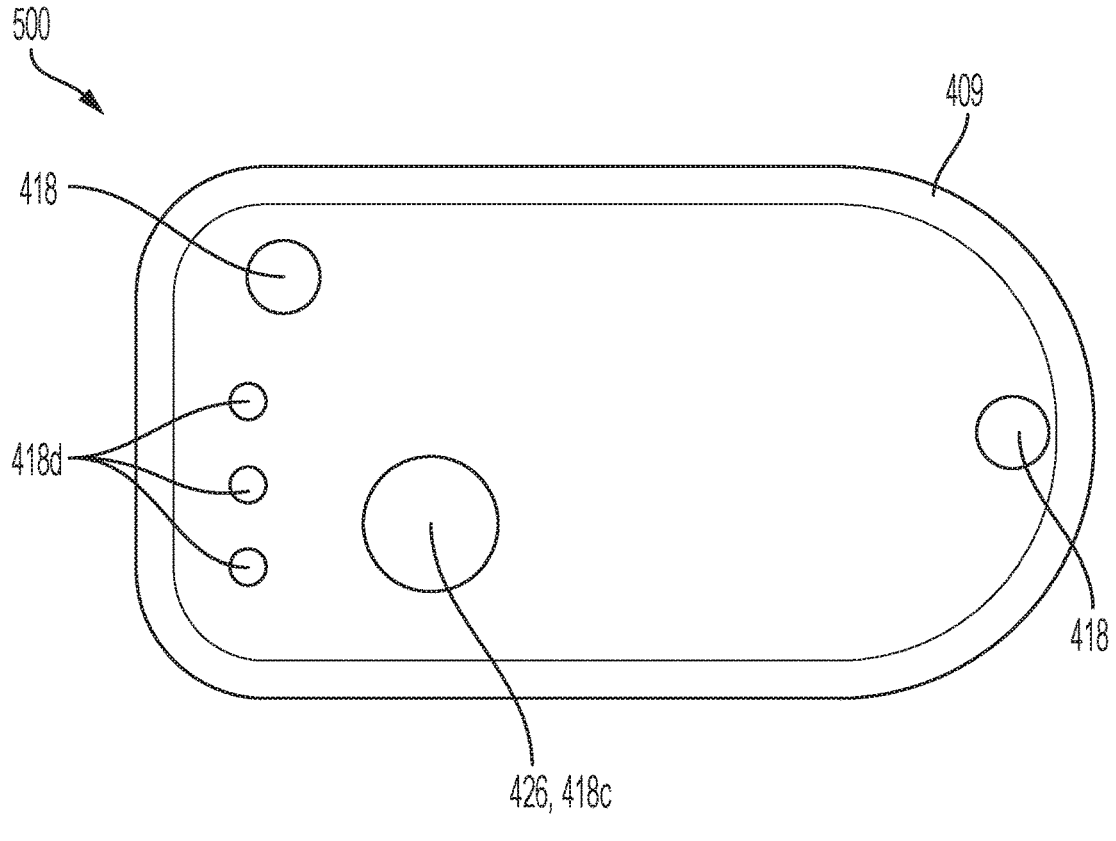
Figure 21C:
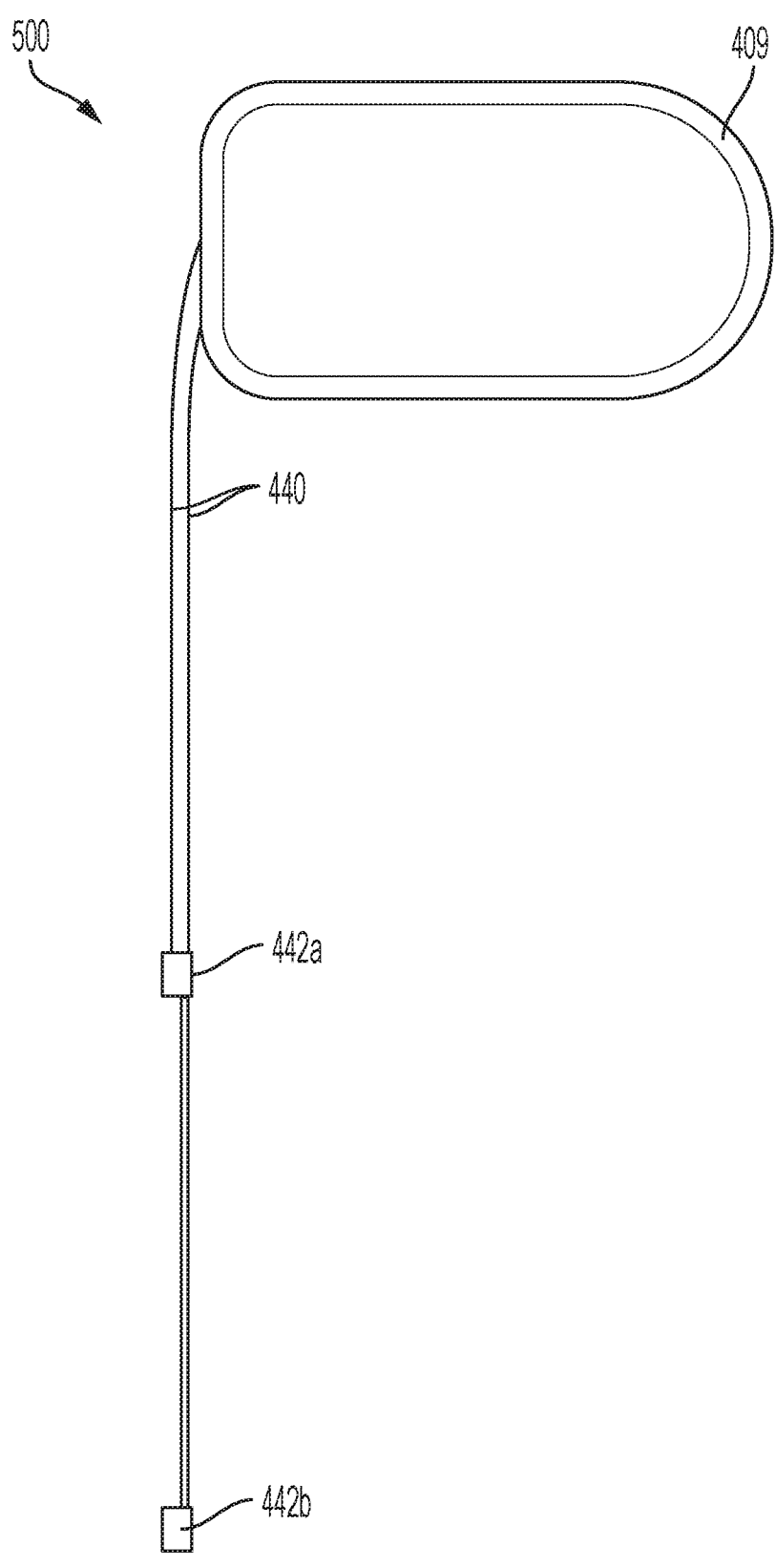
FIG. 21C illustrates a top view of the monitoring device of FIGS. 21A and 21B with EKG leads extending therefrom.

FIGS. 21A and 21B illustrate top and bottom views, respectively, of an implantable patient monitoring device 500, and FIG. 21C illustrates a top view of the monitoring device 500 with EKG leads 440 extending therefrom. As described in more detail below, in various embodiments a patient monitoring device 500 can include several components of the vascular access devices described previously herein, particularly the electronics component 406 (including sensing elements 418) and the battery component 408. However, the monitoring device 500 may operate and be used independently of any vascular access device. For example, such a monitoring device 500 may be implanted concurrently with a vascular access device so as to monitor one or more physiological signals from a patient undergoing treatment using a vascular access device. In some embodiments, the device 500 can be coupled to a vascular access device, or may be implanted adjacent thereto (e.g., within the same pocket). Additionally or alternatively, a patient monitoring device 500 as disclosed herein can be used without any vascular access device. For example, the patient monitoring device can be used to monitor cancer patients who do not have vascular access ports, patients recovering from heart attack, or any other suitable condition.

In some embodiments, a patient monitoring device 500 may include an encasement 409 that can house an electronics component 406 and a battery component 408 similar to any of those described previously herein with respect to FIGS. 1-20B. For example, the electronics component can include a printed circuit board (flexible, rigid, or semi-rigid) or other suitable substrate that supports one or more electronic elements, such as sensing element(s) 418, memory, one or more controllers (e.g., a central processing unit, digital signal processor, application-specific integrated circuit, or any other logic processing unit), wireless communication elements (e.g., wireless communication chip, antennae, etc.), wireless power receivers, and any other suitable electronic elements (e.g., filters, analog-to-digital converters, etc.). In some embodiments, the battery component includes a rechargeable or a non-rechargeable battery configured to provide power to the electronic components. According to some embodiments, the battery component and the electronics component can be combined, co-mounted, or otherwise arranged together as a single unit within the encasement 409. In some embodiments, the encasement 409 can be metallic (e.g., titanium), plastic, medical grade silicone, ceramic, or other suitable material. The encasement 409 can be partially or fully surrounded by or overmolded with a suitable material, for example a flexible biocompatible polymer, silicone, etc.

The device 500 can include any suitable sensing elements 418 housed within or disposed outside the encasement 409. The sensing elements 418 can be configured to obtain one or more physiological measurements while the device 500 is implanted within the body. In some embodiments, the sensing elements 418 can include any of the sensing elements 418 described above with respect to FIGS. 1-20B. For example, the sensing elements 418 can include EKG sensors, temperature sensors, pulse oximeters, accelerometers, magnetometers, pH sensors, and other suitable sensors. In the illustrated embodiment, a plurality of sensing elements 418 are disposed over a lower surface of the encasement 409, and may be configured to be placed in contact with body tissue or fluids when implanted within the body.

The monitoring device 500 can include a window 426 disposed in the lower portion of the encasement 409 and substantially aligned with the pulse oximeter 418c, such that optical signals can be transmitted between the pulse oximeter 418c and adjacent tissue or fluids when the device 400 is implanted within the body. The window 426 can be transparent or translucent, for example being made of sapphire, reinforced glass, or other suitable material that allows transmission of optical signals therethrough.

The encasement 409 can include one or more contacts 441 allowing conductive leads 440 to electrically couple to internal components (e.g., the battery component 408 or portions of the electronics component 406) and any elements exterior to the encasement 409, such as electrodes 442, as shown in FIG. 21C. The leads 440 extend away from the encasement 409 and couple to first and second electrodes 442*a* and 442*b* (collectively "electrodes 442"). When implanted in the body, at least a portion of the leads 440 and the electrodes 442 are in direct contact with bodily tissue or fluids. The electrodes 442 may be electrically coupled to the electronics component via the leads 440.

As noted previously, in some embodiments, the monitoring device 500 may be implanted within a patient to monitor any number of physiological parameters utilizing sensing elements 418 within the electronics component. Accordingly, the monitoring device 500 may be usefully employed beyond the realm of vascular access devices.

Figure 22:
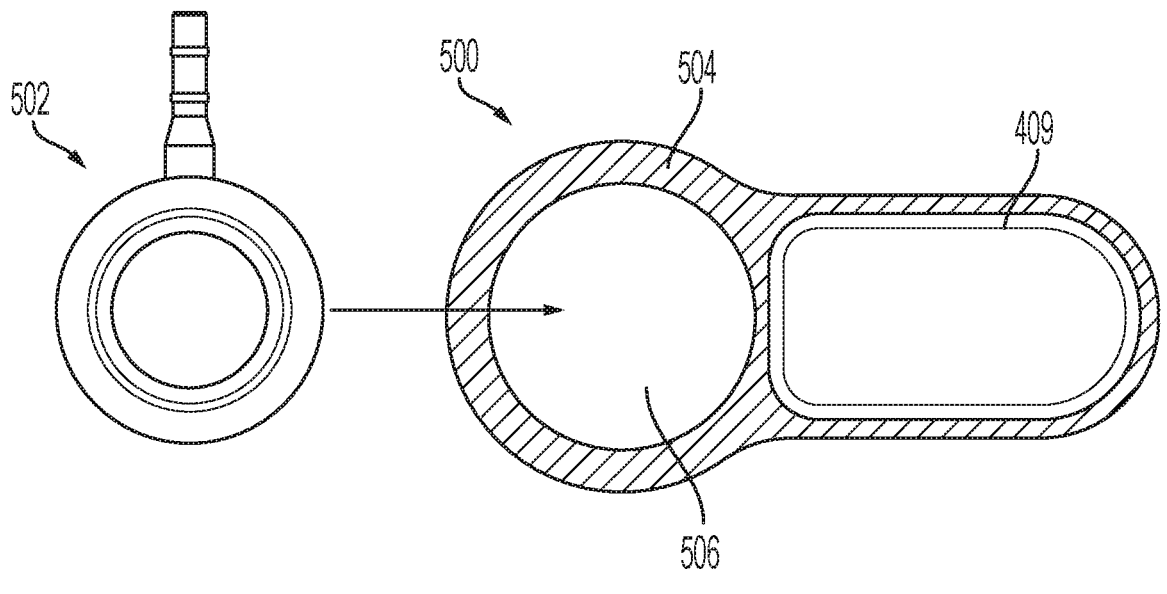
FIG. 22 illustrates a top view of a monitoring device that can be removably coupled with a vascular access device in accordance with the present technology.

As shown in FIG. 22, in some embodiments, a monitoring device 500 can be removably coupled to a vascular access device 502 (e.g., a vascular access port). For example, the monitoring device 500 can be configured to couple with a separate vascular access device 502 or a range of different vascular access devices. This can allow the monitoring device 500 to transform any conventional vascular access device 502 into a smart device, capable of monitoring a number of different physiological parameters. In various embodiments, the monitoring device 500 and the vascular access device 502 can be removably or non-removably (i.e., substantially permanently) coupled together using any suitable means. For example, in the embodiment illustrated in FIG. 22, the device includes an encasement 409 disposed within a surrounding housing 504 that defines a receptable 506. The housing 504 can be made of a biocompatible metal or polymer and configured to retain the encasement 409 therein and to define the receptable 506. In some embodiments, the receptable 506 can be a void, aperture, window, recess, clasp, arms, or any other suitable structure configured to receive and/or interlock with the vascular access device 502. In operation, a vascular access device 502 can be placed within the receptable 506 defined by the housing 504. The assembly (e.g., the monitoring device 500 and the vascular access device 502) can be implanted within the body. Alternatively, the vascular access device 502 can disposed within the receptable 506 or otherwise coupled to the housing 504 after the monitoring device 500 has already been implanted within the body.

For any of the vascular access device and/or monitoring device embodiments detailed above in FIGS. 4A-22, some or all of the encasement 409, the reservoir 404, the septum 414, and the housing 402 may be made from different materials. For example, the encasement 409 may include ceramic, titanium, and/or other materials. The reservoir 404 may include or be entirely formed by one or more biocompatible polymers, such as a thermoplastic polymer (e.g., polyether ether ketone ("PEEK")), and the septum 414 may include or be entirely formed by a biocompatible polymer (e.g., silicone). In those embodiments where both the housing 402 and the septum 414 are made of the same material, such as silicone, the silicone in the septum 414 may be firmer (e.g., have a higher durometer) than the silicone of the housing. Moreover, any of the vascular access device embodiments detailed above in FIGS. 4A-22 may include one or more leads, such as the lead 440 detailed with respect to FIGS. 18A-19B.

CONCLUSION

Although many of the embodiments are described above with respect to vascular access devices for patient monitoring, the technology is applicable to other applications and/or other approaches, such as other types of implantable medical devices (e.g., pacemakers, implantable cardioverter/defibrillators (ICD), deep brain stimulators, insulin pumps, infusion ports, orthopedic devices, and monitoring devices such as pulmonary artery pressure monitors). Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-22.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

25

26

The invention claimed is:

1. A system comprising:
a vascular access device comprising:
    a reservoir component comprising:
        a reservoir body defining an interior chamber configured to receive fluid therein;
        a self-sealing septum covering the chamber; and
        an outlet port in fluid communication with the chamber, the outlet port configured to be mated to a catheter;
a monitoring device removably couplable to the vascular access device, the monitoring device comprising:
    an electronics component comprising:
        one or more sensing elements configured to obtain physiological measurements;
        a wireless communication module; and
        a battery in electrical communication with the sensing element(s) and the wireless communications module; and
a flexible housing configured to enclose the electronics component therein and to removably receive the vascular access device, the flexible housing including one or more topographical features to facilitate localization via palpation, wherein the flexible housing defines a first region for housing the electronics component and a second region for receiving the reservoir component, wherein the first region and the second region are arranged such that the electronics component is maintained separate from the reservoir component when the vascular access device is received in the flexible housing.

2. The system of claim 1, wherein the topographical features comprise a ramped portion over the electronics component, wherein a height of the ramped portion increases along a direction away from the reservoir and increases towards lateral edges of the device.

3. The system of claim 2, wherein the ramped portion is generally u-shaped defining a curved portion concave towards the reservoir component.

4. The system of claim 1, wherein the topographical features further comprise an annular ridge surrounding a circumference of the septum.

5. The system of claim 1, further comprising a suture reinforcement extending along a laterally outward edge of the device and laterally adjacent the reservoir component and/or the electronics component, wherein the suture reinforcement is configured to receive a fixation device therethrough.

6. The system of claim 5, wherein the suture reinforcement is enclosed within the flexible housing.

7. The system of claim 1, further comprising a transparent window disposed in a lower surface of the electronics component, the window aligned with an optical pulse oximeter.

8. The system of claim 1, wherein the electronics component comprises an encasement enclosing the one or more sensing element(s), the wireless communications module, and the battery therein.

9. The system of claim 1, wherein the electronics component comprises an electrical contact configured to be electrically coupled to an electrical lead extending away from the electronics component.

10. The system of claim 9, further comprising the electrical lead coupled to the electrical contact at a first end and an electrode at a second end.

11. The system of claim 9, further comprising a plurality of leads each coupled to an electrical contact of the electronics component and extending away from the electronics component, each lead coupled to a respective electrode.

12. The system of claim 11, wherein the electrodes are configured to measure one or more cardiac parameters.

13. The system of claim 1, wherein the device has a longest transverse dimension of between 30 mm to 70 mm and a greatest thickness of between about 10 mm and 30 mm.

14. The system of claim 1, wherein the one or more sensing elements comprises one or more of: temperature sensing element, a heart rate sensing element, a respiratory rate sensing element, a movement sensing element, a pressure sensing element, an electrical signal sensing element, and an electro-optical sensing element.

15. The system of claim 1, wherein the physiological measurements comprise one or more of: a temperature parameter, an oxygen saturation parameter, a heart rate parameter, a respiratory rate parameter, and an activity level parameter.

16. The system of claim 1, wherein the wireless communications module is configured to wirelessly transmit data using one or more of: near-field communication (NFC), infrared wireless, Bluetooth, ZigBee, Wi-Fi, inductive coupling, or capacitive coupling.

17. The system of claim 1, wherein the housing can flex such that the reservoir component and the electronics component can flex or bend with respect to one another.

18. The system of claim 1, further comprising a wireless recharging unit in electrical communication with the battery.

19. The system of claim 18, wherein the wireless recharging unit comprises a coil.

20. A system comprising:
a vascular access device comprising:
    a reservoir component comprising:
        a reservoir body defining an interior chamber configured to receive fluid therein;
        a self-sealing septum covering the chamber; and
        an outlet port in fluid communication with the chamber, the outlet port configured to be mated to a catheter;
a monitoring device removably couplable to the reservoir component, the monitoring device comprising:
    an electronics component comprising:
        one or more sensing elements configured to obtain physiological measurements;
        a wireless communication module; and
        a battery in electrical communication with the sensing element(s) and the wireless communications module; and
a flexible housing composed of a biocompatible polymer, the flexible housing defining a first receptacle configured for receiving an encasement enclosing the electronics component therein and a second receptacle adjacent to the first receptacle, the second receptacle configured to removably receive the vascular access device therein such that the vascular access device is removably coupled to the monitoring device when the second receptacle receive the vascular access device, wherein the flexible housing comprises one or more topographical features to facilitate localization via palpation.

* * * * *